(12) United States Patent
Tanaka et al.

(10) Patent No.: US 10,973,441 B2
(45) Date of Patent: Apr. 13, 2021

(54) DISPLAY CONTROL DEVICE, DISPLAY CONTROL SYSTEM, DISPLAY CONTROL METHOD, DISPLAY CONTROL PROGRAM, AND RECORDING MEDIUM

(71) Applicant: OMRON CORPORATION, Kyoto (JP)

(72) Inventors: Junichi Tanaka, Kyotanabe (JP); Masatoshi Oba, Tokyo (JP); Fumiji Aita, Nara (JP)

(73) Assignee: OMRON CORPORATION, Kyoto (JP)

( * ) Notice: Subject to any disclaimer, the term of this patent is extended or adjusted under 35 U.S.C. 154(b) by 89 days.

(21) Appl. No.: 15/755,596

(22) PCT Filed: Feb. 21, 2017

(86) PCT No.: PCT/JP2017/006350
§ 371 (c)(1),
(2) Date: Feb. 27, 2018

(87) PCT Pub. No.: WO2017/212690
PCT Pub. Date: Dec. 14, 2017

(65) Prior Publication Data
US 2020/0221977 A1 Jul. 16, 2020

(30) Foreign Application Priority Data
Jun. 7, 2016 (JP) .............................. JP2016-113457

(51) Int. Cl.
*A61B 5/1171* (2016.01)
*A61B 5/00* (2006.01)
(Continued)

(52) U.S. Cl.
CPC .......... *A61B 5/1176* (2013.01); *A61B 5/6889* (2013.01); *A61B 5/744* (2013.01);
(Continued)

(58) Field of Classification Search
None
See application file for complete search history.

(56) References Cited

U.S. PATENT DOCUMENTS

| 6,400,374 B2* | 6/2002 | Lanier ...................... G06F 3/14 345/630 |
| 8,374,438 B1* | 2/2013 | Wagner .................... H04N 5/33 250/330 |

(Continued)

FOREIGN PATENT DOCUMENTS

| CN | 102855470 A | 1/2013 |
| CN | 103988233 A | 8/2014 |

(Continued)

OTHER PUBLICATIONS

Search report, Google.*
(Continued)

*Primary Examiner* — Mohammad J Rahman
(74) *Attorney, Agent, or Firm* — Metrolex IP Law Group, PLLC

(57) ABSTRACT

A display control device (10) comprises an image acquisition component (11), an orientation estimation component (12), and a controller (13). The image acquisition component (11) acquires an infrared image (G1) sensed by infrared array sensors (21a and 21b) installed in a room. The orientation estimation component (12) estimates the orientation of a care receiver (P1) in a room (30) on the basis of the infrared image (G1) acquired by the image acquisition component (11). The controller (13) controls a display device (22) so that a dummy image (D1), which shows a simplified view of the orientation of the care receiver (P1) estimated by the orientation estimation component (12), is displayed superimposed over the infrared image (G1).

19 Claims, 23 Drawing Sheets

(51) Int. Cl.
    *H04N 5/232*          (2006.01)
    *H04N 5/33*           (2006.01)
    *G06T 7/73*           (2017.01)

(52) U.S. Cl.
    CPC ........... *G06T 7/73* (2017.01); *H04N 5/23229*
    (2013.01); *H04N 5/232939* (2018.08); *H04N*
    *5/332* (2013.01); *G06T 2207/10048* (2013.01);
    *G06T 2207/30201* (2013.01)

(56) References Cited

U.S. PATENT DOCUMENTS

| | | | | |
|---|---|---|---|---|
| 8,520,901 | B2* | 8/2013 | Nishimoto | G06F 3/005 348/154 |
| 9,412,161 | B2* | 8/2016 | Varaklis | G16H 20/30 |
| 10,002,460 | B2* | 6/2018 | Black | G06K 9/6221 |
| 2001/0046385 | A1* | 11/2001 | Salapow | H04N 5/2251 396/429 |
| 2006/0008268 | A1* | 1/2006 | Suwa | H04N 13/239 396/310 |
| 2006/0210167 | A1* | 9/2006 | Inoue | G06F 21/32 382/190 |
| 2008/0136916 | A1* | 6/2008 | Wolff | H04N 5/232 348/169 |
| 2008/0244978 | A1* | 10/2008 | Soyugenc | E05F 15/608 49/42 |
| 2010/0098316 | A1* | 4/2010 | Papaioannou | A61B 6/4014 382/132 |
| 2011/0013016 | A1* | 1/2011 | Tillotson | G01W 1/00 348/135 |
| 2011/0058802 | A1* | 3/2011 | Forutanpour | H04N 5/23206 396/225 |
| 2011/0181712 | A1* | 7/2011 | You | G08B 13/1618 348/135 |
| 2012/0290134 | A1* | 11/2012 | Zhao | A61B 90/361 700/259 |
| 2013/0100284 | A1* | 4/2013 | Fujii | A61B 5/1117 348/135 |
| 2013/0243259 | A1* | 9/2013 | Kawaguchi | G06K 9/3241 382/103 |
| 2014/0036129 | A1* | 2/2014 | Nonaka | H04N 5/23293 348/333.02 |
| 2014/0153794 | A1* | 6/2014 | Varaklis | A61B 5/1128 382/128 |
| 2014/0240479 | A1 | 8/2014 | Yasukawa et al. | |
| 2014/0287395 | A1* | 9/2014 | Silverglate | G09B 23/28 434/266 |
| 2014/0300746 | A1 | 10/2014 | Adachi | |
| 2014/0301605 | A1 | 10/2014 | Kawaguchi | |
| 2015/0123966 | A1* | 5/2015 | Newman | G06T 19/006 345/419 |
| 2015/0131777 | A1* | 5/2015 | Makifuchi | A61B 6/463 378/36 |
| 2015/0227328 | A1* | 8/2015 | Yokoyama | H04N 1/00323 358/1.14 |
| 2015/0279083 | A1* | 10/2015 | Pradeep | G06T 7/337 345/419 |
| 2016/0203361 | A1* | 7/2016 | Black | G06K 9/6221 382/203 |
| 2016/0203694 | A1* | 7/2016 | Hogasten | G08B 21/0476 348/164 |
| 2016/0217326 | A1* | 7/2016 | Hosoi | G06K 9/00369 |
| 2016/0231179 | A1* | 8/2016 | Kusukame | G01J 5/047 |
| 2016/0288318 | A1* | 10/2016 | Nakazato | B25J 9/1666 |
| 2016/0302753 | A1* | 10/2016 | Suzuki | A61B 6/56 |
| 2016/0373649 | A1* | 12/2016 | Honda | H04N 5/2253 |
| 2017/0053401 | A1 | 2/2017 | Hata et al. | |
| 2019/0206036 | A1* | 7/2019 | Patriarche | A61B 5/7425 |

FOREIGN PATENT DOCUMENTS

| | | |
|---|---|---|
| JP | 2000-251078 A | 9/2000 |
| JP | 2003-162732 A | 6/2003 |
| JP | 2007-153035 A | 6/2007 |
| JP | 2010-237873 A | 10/2010 |
| JP | 2013-125402 A | 6/2013 |
| JP | 2014-166197 A | 9/2014 |
| JP | 5648840 B2 | 1/2015 |
| JP | 2015-210547 A | 11/2015 |
| JP | 2015-231517 A | 12/2015 |
| JP | 2016-103237 A | 6/2016 |
| KR | 10-2013-0042844 A | 4/2013 |
| WO | 2013/113521 A1 | 8/2013 |

OTHER PUBLICATIONS

Machine translation, Satoshi et al., JP 2010237873 A.*
Machine translation, Tatsumi et al., JP2000251078.*
An English translation of the International Search Report of PCT/JP2017/006350 dated May 9, 2017.
An English translation of the Written Opinion of PCT/JP2017/006350 dated May 9, 2017.
Osamah Rawashdeh et al., "Development of a Low-Cost Fall Intervention System for Hospitalized Dementia Patients", Electro/Information Technology (EIT), 2012 IEEE International Conference on, May 6, 2012, pp. 1-7, IEEE; Relevance is indicated in EESR issued on Sep. 11, 2019.
Pouke Matti, "Using 3D Virtual Environments to Monitor Elderly Patient Activity with Low Cost Sensors", 2013 Seventh International Conference on Next Generation Mobile Apps, Services and Technologies, Sep. 25, 2013, pp. 81-86, IEEE; Relevance is indicated in EESR issued on Sep. 11, 2019.
Ali Larab et al., "A Sustainable Software Architecture for Home Care Monitoring Applications", Digital Ecosystems Technologies (DEST), 2012 6th IEEE International Conference on, Jun. 18, 2012, pp. 1-6, IEEE; Relevance is indicated in EESR issued on Sep. 11, 2019.
The Extended European search report ("EESR") dated Sep. 11, 2019 in a counterpart European Patent application.
The Korean Office Action dated Jan. 11, 2019 in a counterpart Korean Patent application.
The Chinese Office Action dated Oct. 23, 2019 in a counterpart Chinese patent application.

\* cited by examiner

| Region | X direction | Y direction |
|---|---|---|
| RV1 | $0 \leq X \leq 15$ | $0 \leq Y \leq 15$ |
| RV2 | $7 \leq X \leq 9$ | $3 \leq Y \leq 10$ |
| RV3 | $3 \leq X \leq 6$ | $3 \leq Y \leq 10$ |
| RV4 | $0 \leq X \leq 2$ $7 \leq X \leq 15$ $3 \leq X \leq 6$ $3 \leq X \leq 6$ | $0 \leq Y \leq 15$ $0 \leq Y \leq 15$ $0 \leq Y \leq 2$ $11 \leq Y \leq 15$ |

| Region | X direction | Z direction |
|---|---|---|
| RH1 | $0 \leq X \leq 15$ | $0 \leq Z \leq 15$ |
| RH2 | $8 \leq X \leq 10$ | $0 \leq Z \leq 15$ |
| RH3 | $11 \leq X \leq 15$ | $5 \leq Z \leq 9$ |
| RH4 | $11 \leq X \leq 15$ | $7 \leq Z \leq 9$ |
| RH5 | $0 \leq X \leq 10$ | $10 \leq Z \leq 15$ |
| RH6 | $0 \leq X \leq 10$ | $10 \leq Z \leq 12$ |

| Orientation estimated last time | Current orientation candidates |
|---|---|
| not in room (A) | in room (B)<br>not in room (A) (no change) |
| in room (B) | standing next to bed (C)<br>fallen (X)<br>not in room (A)<br>in room (B) (no change) |
| standing next to bed (C) | lying on bed (D)<br>sitting on bed (E)<br>sitting on end of bed (F)<br>fallen (X)<br>in room (B)<br>standing next to bed (C) (no change) |
| lying on bed (D) | sitting on bed (E)<br>sitting on end of bed (F)<br>standing next to bed (C)<br>fallen from bed (first pattern) (Y1)<br>lying on bed (D) (no change) |
| sitting on bed (E) | lying on bed (D)<br>sitting on end of bed (F)<br>standing next to bed (C)<br>fallen from bed (first pattern) (Y1)<br>sitting on bed (E) (no change) |
| sitting on end of bed (F) | lying on bed (D)<br>sitting on bed (E)<br>standing next to bed (C)<br>fallen from bed (second pattern) (Y2)<br>sitting on end of bed (F) (no change) |

FIG. 10

| Orientation | Examination region of first image data | Examination region of second image data | Reference value |
|---|---|---|---|
| not in room (A) | RV1 | RH1 | THA |
| in room (B) | RV1 | RH1 | THB |
| standing next to bed (C) | RV2 | RH2 | THC |
| lying on bed (D) | RV3 | RH4 | THD |
| sitting on bed (E) | RV3 | RH3 | THE |
| sitting on end of bed (F) | RV3 | RH2 | THF |
| fallen (X) | RV4 | RH5 | THX |
| fallen from bed (first pattern) (Y1) | RV2 | RH6 | THY1 |
| fallen from bed (second pattern) (Y2) | RV2 | RH6 | THY2 |

FIG. 11

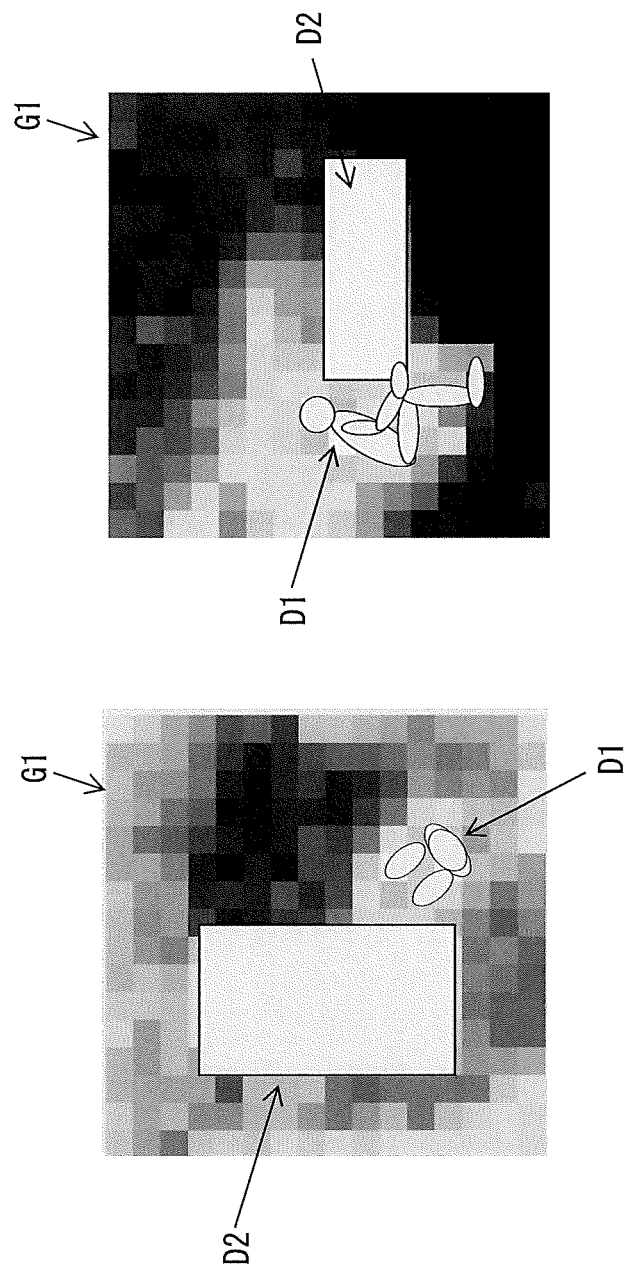

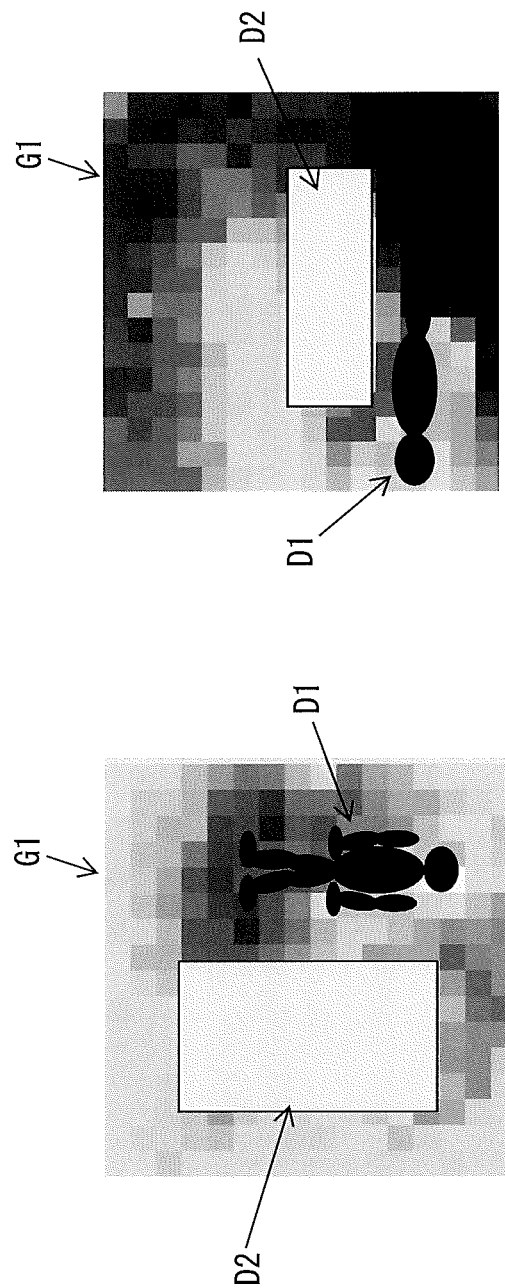

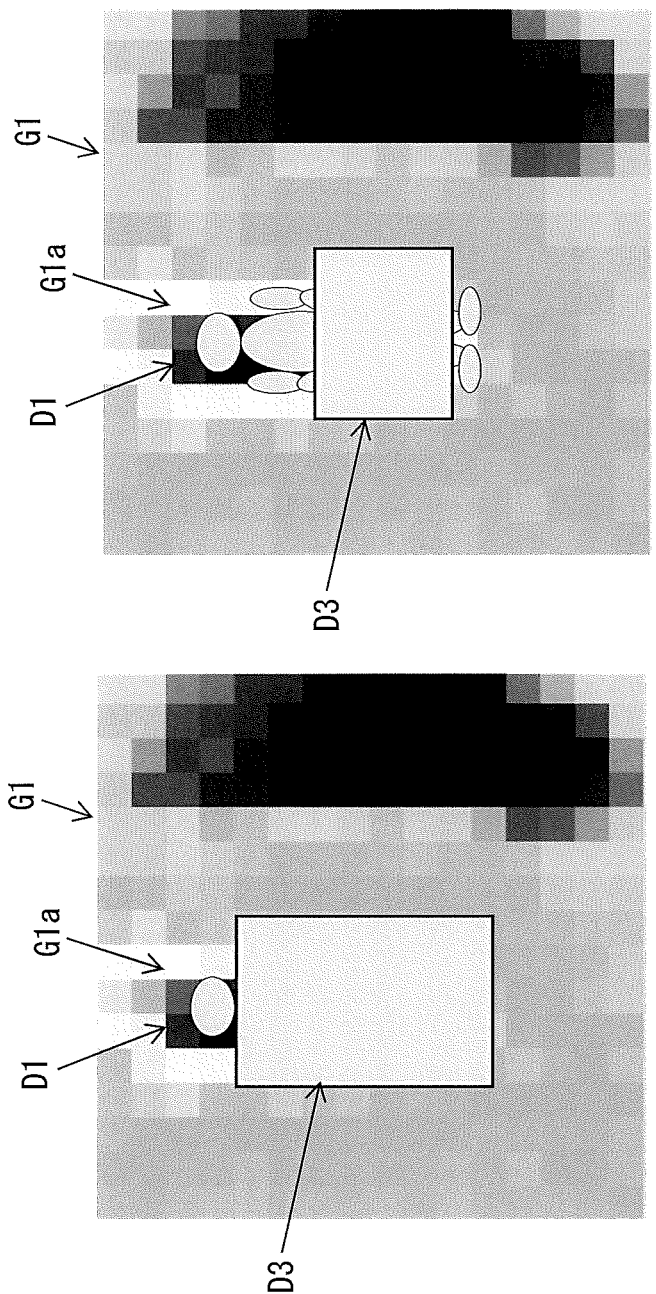

DISPLAY CONTROL DEVICE, DISPLAY CONTROL SYSTEM, DISPLAY CONTROL METHOD, DISPLAY CONTROL PROGRAM, AND RECORDING MEDIUM

FIELD

The present invention relates to a display control device, a display control system, a display control method, a display control program, and a recording medium, with which a situation in which a care receiver needs nursing care is displayed on a display device using a sensing result of an image sensor provided in a room.

BACKGROUND

Recent years have seen the use of an apparatus that monitors the behavior in a room of a person (such as elderly person) who needs nursing care (a care receiver), and displays whether or not it is a situation requiring nursing care.

For example, Patent Literature 1 discloses an orientation estimation device that performs orientation estimation on the basis of statistics for an examination region of image data calculated by referring to information representing a transition model of a person's orientation, and examination information representing an examination region of image data at each orientation in the transition model.

With this orientation estimation device, the orientation of a person can be estimated with less data processing than in a conventional apparatus that makes use of image processing.

However, the following problems are encountered with the above-mentioned conventional orientation estimation device.

With the orientation estimation device disclosed in the above-mentioned publication, although it is possible to estimate the orientation of a care receiver or another such person with just a small amount of data processing, it is difficult to accurately recognize whether or not the care receiver needs nursing care.

CITATION LIST

Patent Literature

Patent Literature 1: JP-A 2015-231517

SUMMARY

Technical Problem

It is an object of the present invention, for example, to provide a display control device, a display control system, a display control method, a display control program, and a recording medium, with which a situation in which a care receiver needs nursing care can be effectively recognized by a caregiver.

Solution to Problem

The display control device according to the first invention comprises an image acquisition component, an orientation estimation component, and a controller. The image acquisition component acquires image data sensed by an image sensor installed in a room. The orientation estimation component estimates the orientation of a person in the room on the basis of the image data acquired by the image acquisition component. The controller controls the display device so that a first dummy image, which shows a simplified view of the orientation of the person estimated by the orientation estimation component, is displayed superimposed over the image data.

Here, in order to watch over a care receiver to check on his or her condition, the orientation of a person (a care receiver, etc.) in the room is estimated by using image data acquired from the image sensor installed in the room, and a first dummy image, which shows a simplified view of the orientation of this person, is superimposed over the image data in the display.

The person inside the room, which is the object of the watching display control, can encompass not only a care receiver who needs nursing care in their daily life, such as an elderly person or a physically handicapped person, but also healthy persons, pets (animals), and so forth.

The number of image sensors installed in the room may be one or more. Possible places where the image sensor is installed include locations that allow for the sensing of the care receiver or the like in the room, such a on the ceiling or on a wall. The image sensor may be an image pickup device such as a surveillance camera, or may be an infrared sensor, a distance sensor, or the like.

Also, orientation estimation using image data may be performed, for example, using a known method in which a statistical amount is calculated in an examination region of image data using a transition model of the orientation of the person, and the orientation of the person at the current time is estimated from the orientation of the person at a previous point in time on the basis of the statistical amount (see Patent Literature 1).

The first dummy image is an image showing a simplified view of the shape of the person corresponding to the estimated orientation of the person, and a number of different images corresponding to a plurality of orientations, such as a standing position, a seated position, and a recumbent position, are prepared. The first dummy images may be stored in a storage means within the device, or in an external device (server, cloud, etc.), in a state of being associated with each orientation.

Also, when it is used in a nursing facility, a hospital, or the like, the display device whose display is controlled by the controller can be, for example, a monitor in a central control room in which a caregiver or a nurse is always present, or a portable terminal carried around by a caregiver or nurse.

This allows the controller to control the display device so that a first dummy image corresponding to the orientation estimated by the orientation estimation component is displayed superimposed over the image data acquired by the image acquisition component.

Thus, a caregiver or the like who looks at the display on the display device, for example, will see the first dummy image that shows the simplified orientation of the care receiver or the like displayed on the display device, and can effectively and accurately recognize whether or not the care receiver needs care.

The display control device according to the second invention is the display control device according to the first invention, further comprising a storage component that stores a plurality of first dummy images in a state of being associated with orientations of the person.

Here, a storage component for storing a plurality of first dummy images is provided inside the device.

Consequently, the controller can extract the first dummy image corresponding to the orientation estimated by the orientation estimation component from among the plurality of first dummy images stored in the storage component in the device, and display this superimposed over the image data.

The display control device according to the third invention is the display control device according to the first or second invention, wherein the controller superimposes and displays the head or face portion of the first dummy image, using as a reference the position of the head or face of the person included in the image data.

Here, when a dummy image is superposed over the image data, the position of the head or face of the person detected in the image data is used as a reference to give a superimposed display of the position of the head or face of the first dummy image.

Here, the detection of the head or the face in the image data can be set, for example, by detecting the eye position if it is a camera image, the position where the temperature is high if it is an infrared image, or the like.

This makes it possible to superimpose the first dummy image selected according to the orientation of the person over the image data, using the head or face portion as a reference.

The display control device according to the fourth invention is the display control device according to any of the first to third inventions, further comprising a determination component that refers to the plurality of pieces of image data continuously acquired by the image acquisition component, and determines a care urgency level according to the amount of flickering of an image near the person in the image data.

Here, whether or not the person (the care receiver) included in the image data needs care is determined from how much flickering there is of the image near the person in the image data, using image data such as a moving picture continuously acquired by the image acquiring component.

Here, whether or not care is necessary can be determined, for example, by determining that at least a predetermined length of time has elapsed in a state in which almost no flickering is seen of the image near the person in the continuously acquired image data for a seated care receiver.

Conversely, with a seated care receiver, if flickering is seen in the image near the person in the continuously acquired image data, it can be concluded that the care receiver is changing clothes, is operating a portable terminal, or is in some other such state that does not require nursing care.

Consequently, by referring to the flickering of the image in continuously acquired image data such as a moving picture, it is possible to determine whether or not the care receiver needs nursing care, more accurately than with a determination based on the orientation of the care receiver.

The display control device according to the fifth invention is the display control device according to the fourth invention, wherein the image sensor is an infrared sensor that acquires a thermal image. The determination component makes a determination according to the degree of fluctuation in the position of the thermal center of gravity in an area near the person in the thermal image continuously acquired by the infrared sensor.

Here, if an infrared sensor is used as the image sensor, when making a determination based on the flickering of the image in the continuously acquired image data, determination is made according to the fluctuation of the position of the thermal center of gravity in the thermal image acquired by the infrared sensor.

Thus, even when an infrared sensor is used as the image sensor, it can be determined that care is needed by taking advantage of the characteristics of the thermal image, such as when the change in the position of the thermal center of gravity is below a certain threshold.

Conversely, if the change in the position of the thermal center of gravity is above a certain threshold value, it can be determined that care is needed, such as when the care receiver is changing clothes, or when a mobile terminal is being operated, for example.

The display control device according to the sixth invention is the display control device according to the fourth invention, wherein the image sensor is an infrared sensor that acquires a thermal image. The determination component makes a determination by detecting enlargement of a heat source in an area near the person in the thermal image continuously acquired by the infrared sensor.

Here, if an infrared sensor is used as the image sensor, a determination is made by detecting enlargement of a heat source in the continuously acquired image data.

Consequently, the thermal image continuously acquired by the infrared sensor can be used to apprise the caregiver that the care receiver has vomited, for example.

The display control device according to the seventh invention is the display control device according to any of the first to sixth inventions, further comprising a count estimator that estimates the number of people included in the image data acquired by the image acquisition component.

Here, the count estimator estimates the number of people in the room detected by the image sensor.

Consequently, when the care receiver resides in a private room, for example, it will be possible to estimate whether or not a person other than the care receiver is in the room.

Alternatively, in the case of a room in which a plurality of care receivers reside, for example, it can be estimated whether or not there are more people than the number of residents.

The display control device according to the eighth invention is the display control device according to the seventh invention, wherein the controller performs display control when it has been determined, as a result of estimation by the count estimator, that the number of people in the image data is one.

Here, if a care receiver resides in a private room, for example, if it is presumed that a family member, a friend, or a caregiver is in the room along with the care receiver when it has been presumed that someone other than the care receiver is in the room.

Accordingly, since it is presumed that there is someone in the room who can care for the care receiver, a situation such as this can be excluded from watching display control.

The display control device according to the ninth aspect of the invention is the display control device according to any of the first to eighth inventions, wherein the controller changes the color of the first dummy image on the display device according to the estimation result produced by the orientation estimation component.

Here, if the result of estimation by the orientation estimation component leads to the presumption that a care receiver is lying down in a location other than on the bed in the room, for example, it is determined that care is required, and the color of the first dummy image is changed to a color different from the one used ordinarily, to make it clear that there is an emergency.

Here, the color of the first dummy image is, for example, preferably displayed in black and white normally, and is changed to red, yellow, or the like in case of an emergency that would require care.

Consequently, the caregiver or other person who sees the display on the display device can easily tell whether there is an emergency.

The display control device according to the tenth invention is the display control device according to any of the first to ninth inventions, wherein the controller flashes the first dummy image on the display device according to the estimation result produced by the orientation estimation component.

Here, if the result of estimation by the orientation estimation component leads to the presumption that a care receiver is lying down in a location other than on the bed in the room, for example, it is determined that care is required, and the first dummy image is flashed, to make it clear that there is an emergency.

Consequently, the caregiver or other person who sees the display on the display device can easily tell whether there is an emergency.

The display control device according to the eleventh invention is the display control device according to any of the first to tenth inventions, wherein the controller displays the first dummy image superimposed over the image data and displays an emergency message on the display device, according to the estimation result produced by the orientation estimation component.

Here, when displaying the first dummy image selected by orientation estimation superimposed over the image data, if it has been determined that there is a need for nursing care, for example, an urgent message is displayed on the display device along with the image data.

This allows the caregiver or the like to tell that there is an emergency from text information together with image information.

The display control device according to the twelfth invention is the display control device according to any of the first to eleventh inventions, wherein the orientation estimation component estimates the orientation by using detection results produced by the plurality of the image sensors, which detect a person who is the room from different directions.

Here, a plurality of image sensors for detecting something within a room from different directions (such as upward, lateral, etc.) are used as the image sensor installed in the room.

Consequently, since a plurality of sets of image data having different sensing directions can be used as the image data used for orientation estimation, it is possible to more accurately estimate the orientation of a person such as a care receiver.

The display control device pertaining to the thirteenth invention is the display control device according to any of the first to twelfth inventions, wherein the controller displays the first dummy image, corresponding to at least one of a standing position, a seated position, a recumbent position, a lateral recumbent position, a prone position, and a half-sitting position of the person, superimposed over the image data.

Here, a first dummy image is used which corresponds to at least one of the orientations of the person estimated by the orientation estimation component, namely, a standing position, a seated position, a recumbent position, a lateral recumbent position, a prone position, and a half-sitting position.

Consequently, it is possible, for example, to estimate the orientation of a care receiver or the like in a subdivided state, and to display the corresponding first dummy image superimposed over the image data.

The display control device according to the fourteenth invention is the display control device according to any of the first to thirteenth inventions, wherein a second dummy image corresponding to furniture and equipment installed in the room is displayed so as to be superimposed with the locations of the furniture and the equipment in the image data.

Here, in addition to a plurality of first dummy images corresponding to the various orientations of a person, a second dummy image corresponding to furniture and equipment installed in the room is displayed on the display device so as to be superimposed over the image data.

Consequently, if the positions of a bed, a blanket, a chest of drawers, a table, a chair, a portable toilet, and the like installed in the room are displayed superimposed, for example, it will be easier to estimate what the caregiver in the room is doing, and where the caregiver is doing it.

The display control system according to the fifteenth invention comprises the display control device according to any of the first to fourteenth inventions, and an image sensor that supplies the image data to the image acquisition component.

Here, a display control system is configured to include the display control device described above and an image sensor installed in a room.

Consequently, as described above, the system can be configured, for example, so that the caregiver or the like looks at the first dummy image indicating the orientation of the care receiver or the like displayed on the display device, and can effectively and accurately recognize whether or not the care receiver is in need of nursing care.

The display control system pertaining to the sixteenth invention is the display control system according to the fifteenth invention, further comprising a display device whose display is controlled by the controller of the display control device.

Here, a display control system is configured to include the above-mentioned display control device, image sensor, and display device.

Consequently, as discussed above, the system is configured, for example, so that the caregiver or the like can use the display device to check the first dummy image indicating the orientation of the care receiver or the like displayed on the display device, and to effectively and accurately recognize whether or not the care receiver needs nursing care.

The display control system according to the seventeenth invention is the display control system according to the sixteenth invention, wherein the display device includes the display device of the host terminal used by the caregiver who cares for the person who is in the room, or a portable terminal owned by the caregiver.

Here, a host terminal installed in a central control room used by a caregiver, or a mobile terminal owned by a caregiver is used, for example, as the display device whose display is controlled by the controller.

Consequently, for example, the caregiver or the like can easily recognize whether or not the care receiver in the room is in need of nursing care by looking at the image data over which the first dummy image is superimposed, on the host terminal, a mobile terminal, or the like.

The display control system according to the eighteenth invention is the display control system according to any of the fifteenth to seventeenth inventions, wherein the image sensor includes a first image sensor for detecting the person from above in the room, and a second image sensor for detecting the person from the side.

Here, two image sensors for sensing inside the room from above and from the side are used as the image sensor installed in the room.

Consequently, since two types of image data having different detection directions can be used as the image data used for orientation estimation, the orientation of a person such as a care receiver can be estimated more accurately.

The display control system according to the nineteenth invention is the display control system according to any of the fifteenth to eighteenth inventions, wherein the image sensor is either an infrared array sensor or a distance sensor.

Here, either an infrared array camera or a distance sensor is used as the image sensor installed in the room.

Consequently, compared to when a surveillance camera or another such imaging device is used as the image sensor, the processing load is lighter in orientation estimation and in the superimposition of the first dummy image.

Also, since it is difficult to identify individuals such as care receivers and caregivers detected by the image sensor, this eliminates the problem of maintaining the privacy of the care receiver, caregiver, or the like.

The display control method according to the twentieth invention comprises an image acquisition step, an orientation estimation step, and a control step. In the image acquisition step, image data detected by an image sensor installed in a room is acquired. In the orientation estimation step, the orientation of a person in the room is estimated based on the image data acquired in the image acquisition step. In the control step, the display device is controlled so that a first dummy image, which shows a simplified view of the orientation of the person as estimated in the orientation estimation step, is superimposed over the image data.

Here, for example, in order to confirm the state of a care receiver, the orientation of a person (such as a care receiver) in the room is estimated by using the image data acquired from the image sensor installed in the room, and the first dummy image that shows a simplified version of that orientation is displayed superimposed over the image data.

Here, a single image sensor or two or more image sensors may be installed in the room. Possible installation locations for the image sensor include a location from which the care receiver or the like in the room can be detected, such as on the ceiling or a wall. The image sensor may be an image pickup device such as a surveillance camera, or an infrared sensor, a distance sensor, or the like may be used.

Also, orientation estimation using image data may be accomplished, for example, by using a known method of calculating a statistical amount in an examination region of image data using a transition model of the orientation of a person, and estimating the orientation of the person at the current time from the orientation of the person the last time on the basis of this statistical amount (see Patent Literature 1).

The first dummy image is an image showing the simplified shape of a person corresponding to the estimated orientation of the person, and a number of different images corresponding to a plurality of orientations, such as a standing position, a seated position, and a recumbent position, are prepared. The first dummy images may be stored in a storage means in the device, or in an external device (a server, a cloud, etc.), in a state of being associated with the orientations.

Also, as the display device whose display is controlled in the control step, when it is used in a nursing facility, a hospital, or the like, for example, a monitor in a central control room that is always staffed by a caregiver or a nurse, a portable terminal carried around by a caregiver or a nurse, or the like can be used.

Consequently, in the control step, the display device can be controlled so that the first dummy image corresponding to the orientation estimated in the orientation estimation step is displayed superimposed over the image data acquired in the image acquisition step.

Therefore, for example, a caregiver or the like who looks at the display on the display device will see the first dummy image that shows a simplified view of the orientation of the care receiver or the like displayed on the display device, and can effectively and accurately recognize whether or not the care receiver needs nursing care.

The display control program according to the twenty-first invention causes a computer to execute a display control method comprising an image acquisition step, an orientation estimation step, and a control step. The image acquisition step involves acquiring image data sensed by an image sensor installed in a room. The orientation estimation step involves estimating the orientation of a person in the room on the basis of the image data acquired in the image acquisition step. The control step involves controlling a display device so that a first dummy image, which shows a simplified view of the orientation of the person estimated in the orientation estimation step, is displayed superimposed over the image data.

Here, with a display control program that causes a computer to execute the above-mentioned display control method, for example, in order to check on the state of a care receiver, the orientation of the person in the room (the care receiver, etc.) is estimated using the image data acquired from the image sensor installed in the room, and a first dummy image that shows a simplified view of the orientation is displayed superimposed over the image data.

Here, a single image sensor or two or more image sensors may be installed in the room. Possible installation locations for the image sensor include a location from which the care receiver or the like in the room can be detected, such as on the ceiling or a wall. The image sensor may be an image pickup device such as a surveillance camera, or an infrared sensor, a distance sensor, or the like may be used.

Also, orientation estimation using image data may be accomplished, for example, by using a known method of calculating a statistical amount in an examination region of image data using a transition model of the orientation of a person, and estimating the orientation of the person at the current time from the orientation of the person the last time on the basis of this statistical amount (see Patent Literature 1).

The first dummy image is an image showing the simplified shape of a person corresponding to the estimated orientation of the person, and a number of different images corresponding to a plurality of orientations, such as a standing position, a seated position, and a recumbent position, are prepared. The first dummy images may be stored in a storage means in the device, or in an external device (a server, a cloud, etc.), in a state of being associated with the orientations.

Also, as the display device whose display is controlled in the control step, when it is used in a nursing facility, a hospital, or the like, for example, a monitor in a central control room that is always staffed by a caregiver or a nurse, a portable terminal carried around by a caregiver or a nurse, or the like can be used.

Consequently, in the control step, the display device can be controlled so that the first dummy image corresponding to the orientation estimated in the orientation estimation step is displayed superimposed over the image data acquired in the image acquisition step.

Therefore, for example, a caregiver or the like who looks at the display on the display device will see the first dummy image that shows a simplified view of the orientation of the care receiver or the like displayed on the display device, and can effectively and accurately recognize whether or not the care receiver needs nursing care.

The recording medium according to the twenty-second invention stores a display control program for causing a computer to execute a display control method comprising an image acquisition step, an orientation estimation step, and a control step. The image acquisition step involves acquiring image data sensed by an image sensor installed in a room. The orientation estimation step involves estimating the orientation of a person in the room on the basis of the image data acquired in the image acquisition step. The control step involves controlling a display device so that a first dummy image, which shows a simplified view of the orientation of the person estimated in the orientation estimation step, is displayed superimposed over the image data.

Here, with a recording medium that stores a display control program for causing a computer to execute the above-mentioned display control method, in order to check on the state of a care receiver, for example, image data acquired from an image sensor installed in the room is used to estimate the orientation of a person who is in the room (such as a care receiver), and a first dummy image that shows a simplified view of the orientation is displayed superimposed over the image data.

The number of image sensors installed in the room may be one or more. Possible places where the image sensor is installed include locations that allow for the sensing of the care receiver or the like in the room, such a on the ceiling or on a wall. The image sensor may be an image pickup device such as a surveillance camera, or may be an infrared sensor, a distance sensor, or the like.

Also, orientation estimation using image data may be performed, for example, using a known method in which a statistical amount is calculated in an examination region of image data using a transition model of the orientation of the person, and the orientation of the person at the current time is estimated from the orientation of the person at a previous point in time on the basis of the statistical amount (see Patent Literature 1).

The first dummy image is an image showing a simplified view of the shape of the person corresponding to the estimated orientation of the person, and a number of different images corresponding to a plurality of orientations, such as a standing position, a seated position, and a recumbent position, are prepared. The first dummy images may be stored in a storage means within the device, or in an external device (server, cloud, etc.), in a state of being associated with each orientation.

Also, when it is used in a nursing facility, a hospital, or the like, the display device whose display is controlled in the control step can be, for example, a monitor in a central control room in which a caregiver or a nurse is always present, or a portable terminal carried around by a caregiver or nurse.

Consequently, in the control step, the display device can be controlled so that a first dummy image corresponding to the orientation estimated in the orientation estimation step is displayed superimposed over the image data acquired in the image acquisition step.

Thus, a caregiver or the like who looks at the display on the display device, for example, will see the first dummy image that shows the simplified orientation of the care receiver or the like displayed on the display device, and can effectively and accurately recognize whether or not the care receiver needs care.

Advantageous Effects

With the display control device according to the present invention, for example, it is possible for a caregiver to effectively recognize a situation in which a care receiver needs care.

BRIEF DESCRIPTION OF THE DRAWINGS

FIG. 10 is a diagram illustrating the transition model information in FIG. 9;

FIG. 11 shows region information indicating the examination regions of the first and second image data for each of the orientations in the transition model in FIG. 9, and reference value information representing reference values for determining whether there has been a transition to each orientation;

FIGS. 16A and 16B show a seated image captured using two infrared array sensors (on the ceiling and to the side) installed in the room shown in FIG. 2;

FIGS. 19A and 19B show a rolled-over recumbent image (emergency) captured using two infrared array sensors (on the ceiling and to the side) installed in the room shown in FIG. 2;

FIG. 22A is a diagram showing a recumbent image (with vigorous flickering) captured using an infrared array sensor installed on the ceiling of the room shown in FIG. 2, and FIG. 22B is a diagram showing a recumbent image (blanket turned down, vigorous flickering) captured using an infrared array sensor installed on the ceiling of the room shown in FIG. 2;

DETAILED DESCRIPTION

A display control device 10 according to an embodiment of the present invention, and a display control system 20 comprising this device, will be described below through reference to FIGS. 1 to 23.

1. Configuration of Display Control System 20

Figure 1:
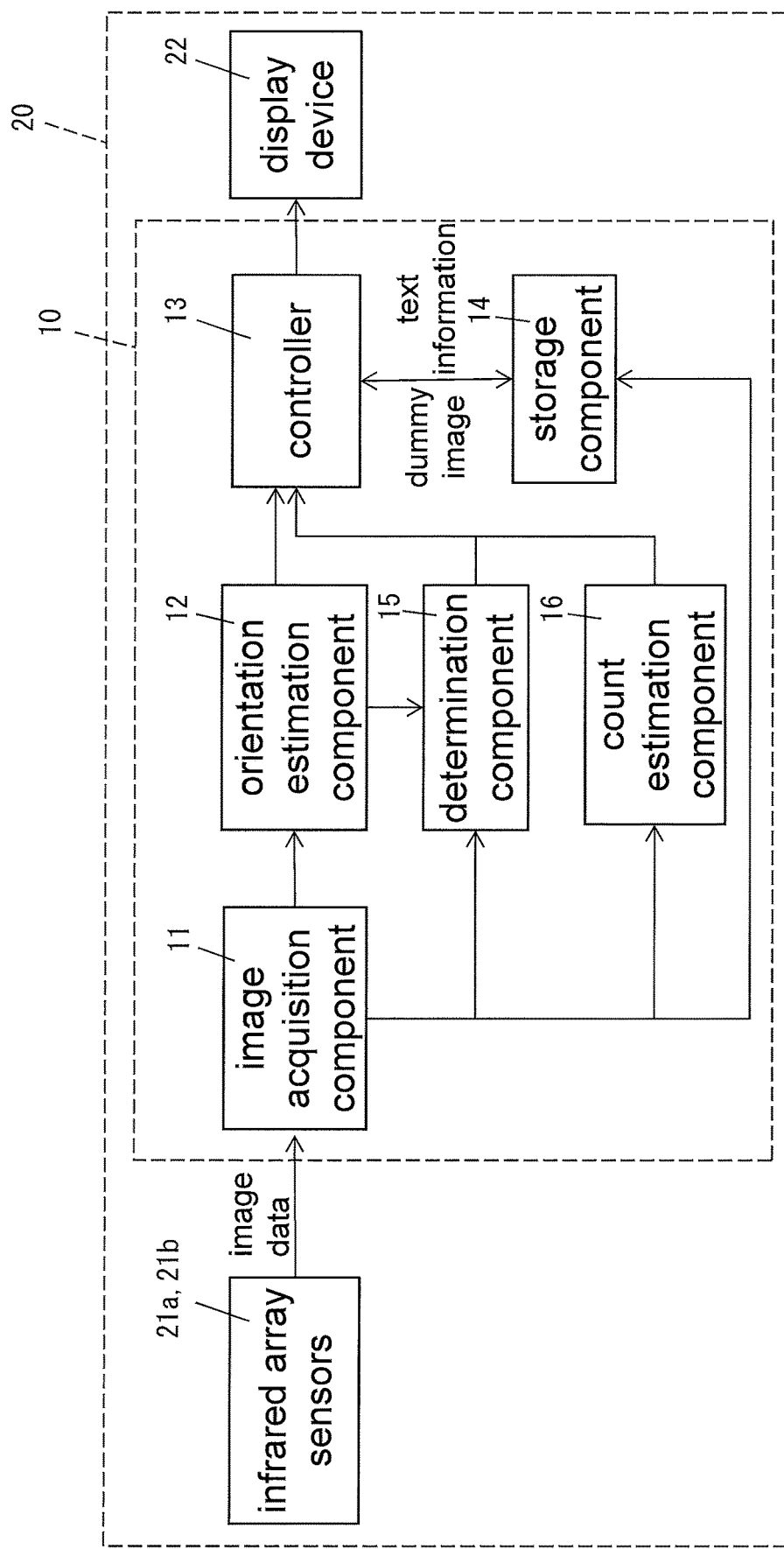
FIG. 1 is a block diagram of the configuration of a display control system including the display control device according to an embodiment of the present invention.

The display control system 20 according to this embodiment is, for example, a system for monitoring a care receiver in need of nursing care in his everyday activities, such as in a nursing home or a hospital, and allowing a caregiver to accurately recognize the state of the c are receiver. As shown in FIG. 1, the display control system 20 comprises the display control device 10, infrared array sensors 21a and 21b, and a display device 22.

Figure 2:
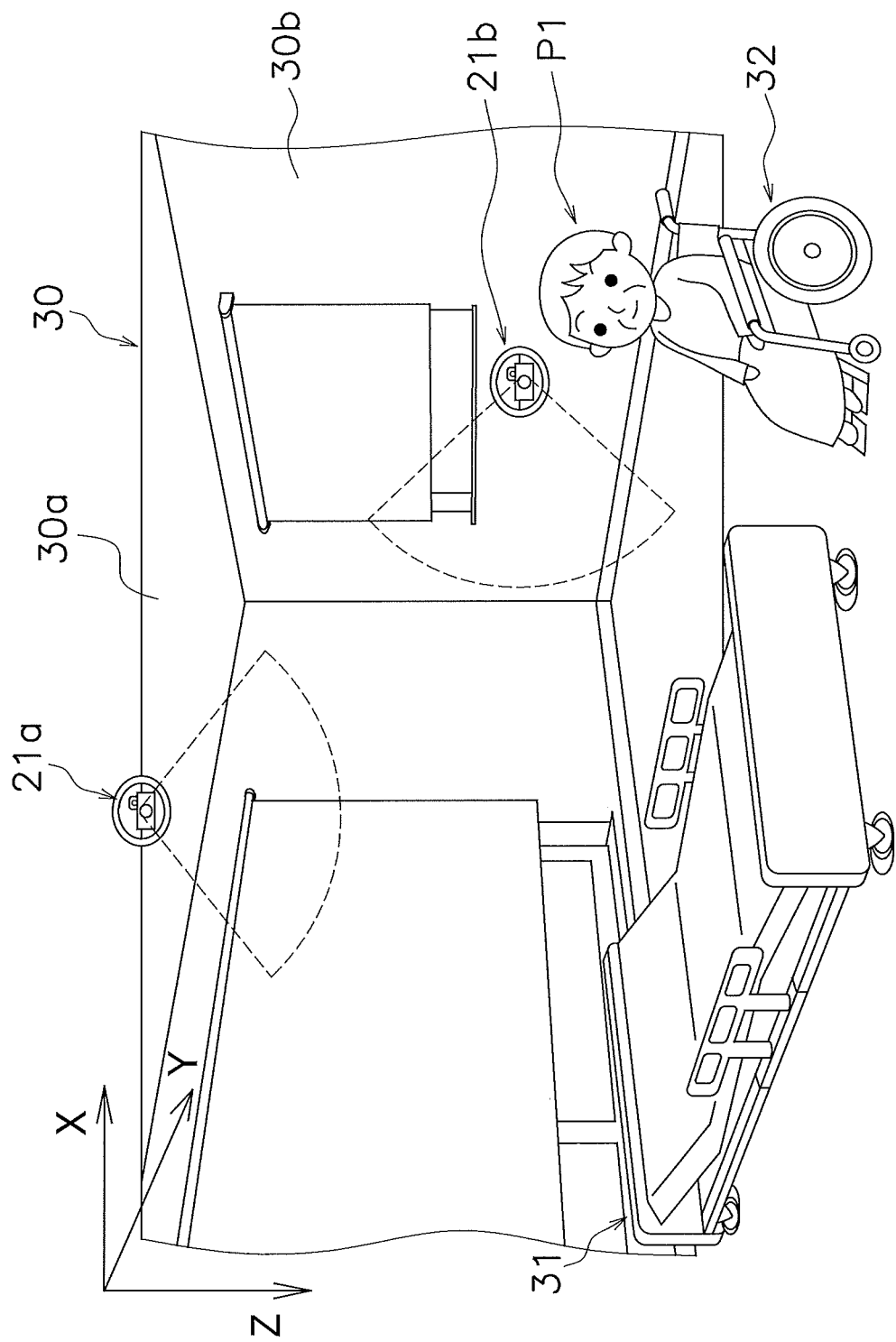
FIG. 2 is an oblique view of the configuration in a room where an image is acquired that is displayed on the display device with the display control system in FIG. 1.

Here, with the display control system 20 in this embodiment, in order to watch over the care receiver (person) P1 in a room 30, as shown in FIG. 2, the system makes use of the two infrared array sensors 21a and 21b, which are capable of capturing images of the care receiver P1 from above and from the side in the room 30.

A bed 31, a wheelchair 32, and other such in-room equipment are installed in the room 30, forming the living space of the care receiver P1. A coordinate system X-Y-Z of the inside of the room is shown in FIG. 2.

The display control device 10 uses an infrared image G1 (see FIG. 12) captured by the infrared array sensors 21a and 21b to determine whether or not the care receiver P1 in the room 30 needs care, and displays the result on the display device 22. The configuration of the display control device 10 will be described below in more detail.

Here, with the display control device 10 in this embodiment, the infrared image G1 (see FIG. 12) is used in order to watch over the care receiver P1 in the room 30. Consequently, compared to when the watching is performed using a surveillance camera image, for example, watching can be performed while protecting the privacy of the care receiver P1.

The infrared array sensors 21a and 21b are designed so that the portion of a person's face in the captured infrared image G1 taken is made up of 2 to 6 pixels. Consequently, an individual cannot be identified even with individual recognition technology using a portion of a face in an image, for example, which allows someone to watch over the care receiver P1 while still protecting the privacy of the care receiver.

As shown in FIG. 2, the infrared array sensors 21a and 21b are attached to the ceiling 30a in the room 30, and capture images of the care receiver P1 in the room 30 from above.

Figure 3B:
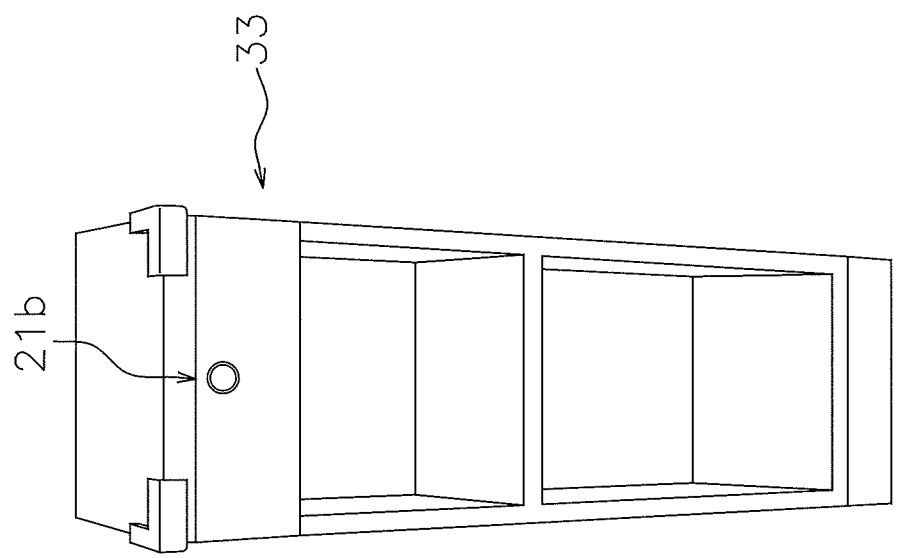
FIG. 3B is a diagram showing an infrared array sensor attached to a shelf in the room shown in FIG. 2.
Figure 3A:
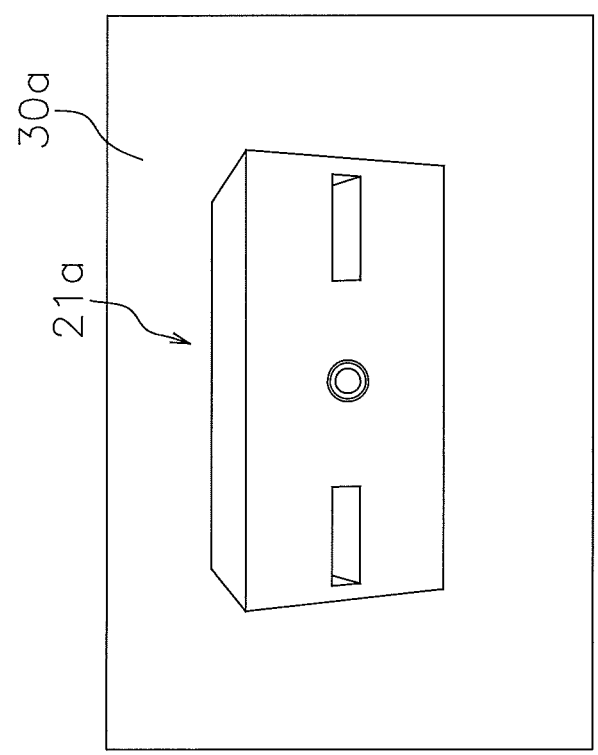
FIG. 3A is a diagram showing an infrared array sensor attached to the ceiling of the room shown in FIG. 2.
Figure 4B:
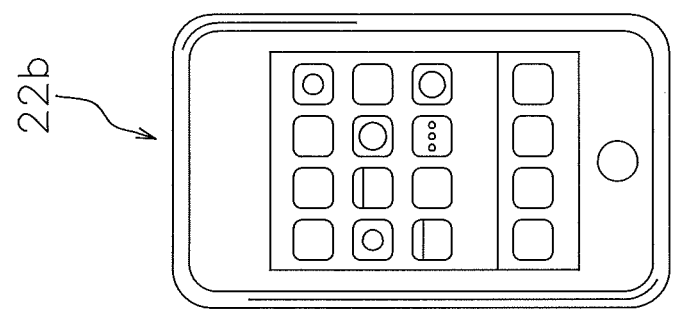
FIGS. 4A and 4B are diagrams showing an example of a display device that constitutes the display control system in FIG. 1 (a host computer and a portable terminal)
Figure 4A:
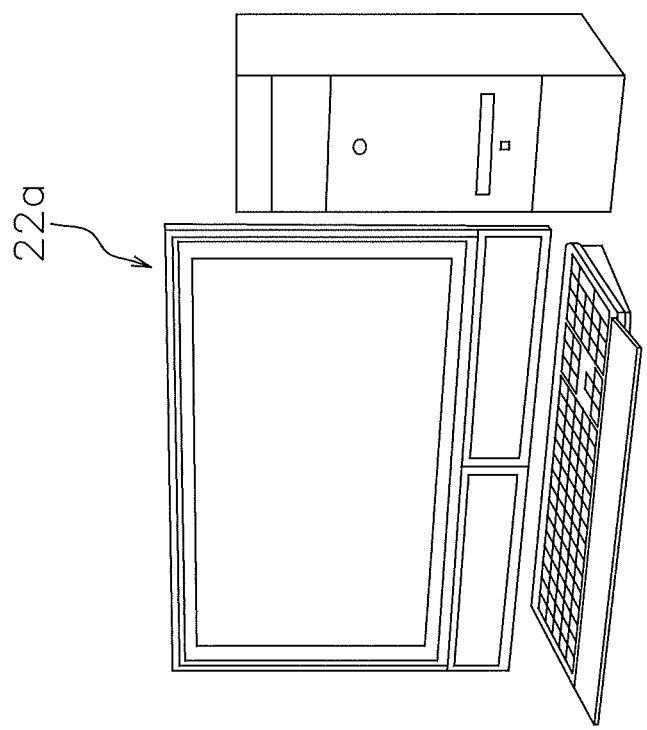

As shown in FIG. 3A, the infrared array sensor (first image sensor) 21a is fixed directly to the ceiling 30a of the chamber 30.

As shown in FIG. 2, the infrared array sensor 21b (second image sensor) is attached to the wall 30b in the room 30, and captures images of the care receiver P1 in the room 30 from the side.

As shown in FIG. 3B, rather than being installed on the wall 30b, the infrared array sensor 21b may be embedded in something within the room, such as a shelf 33.

The infrared image data acquired by the infrared array sensors 21a and 21b is transmitted to the image acquisition component 11 of the display control device 10.

The infrared image data captured by the infrared array sensors 21a and 21b is such that the temperature of the image region increases the higher is the pixel value, and the temperature of the image region decreases the lower is the pixel value. That is, since an area where a person is located will have a higher temperature, the value of pixels in an area where a person was imaged will be higher. Thus, an area where a person is present (a region of higher temperature) can be identified from the infrared image data by finding an area with higher pixel values.

Figure 12:
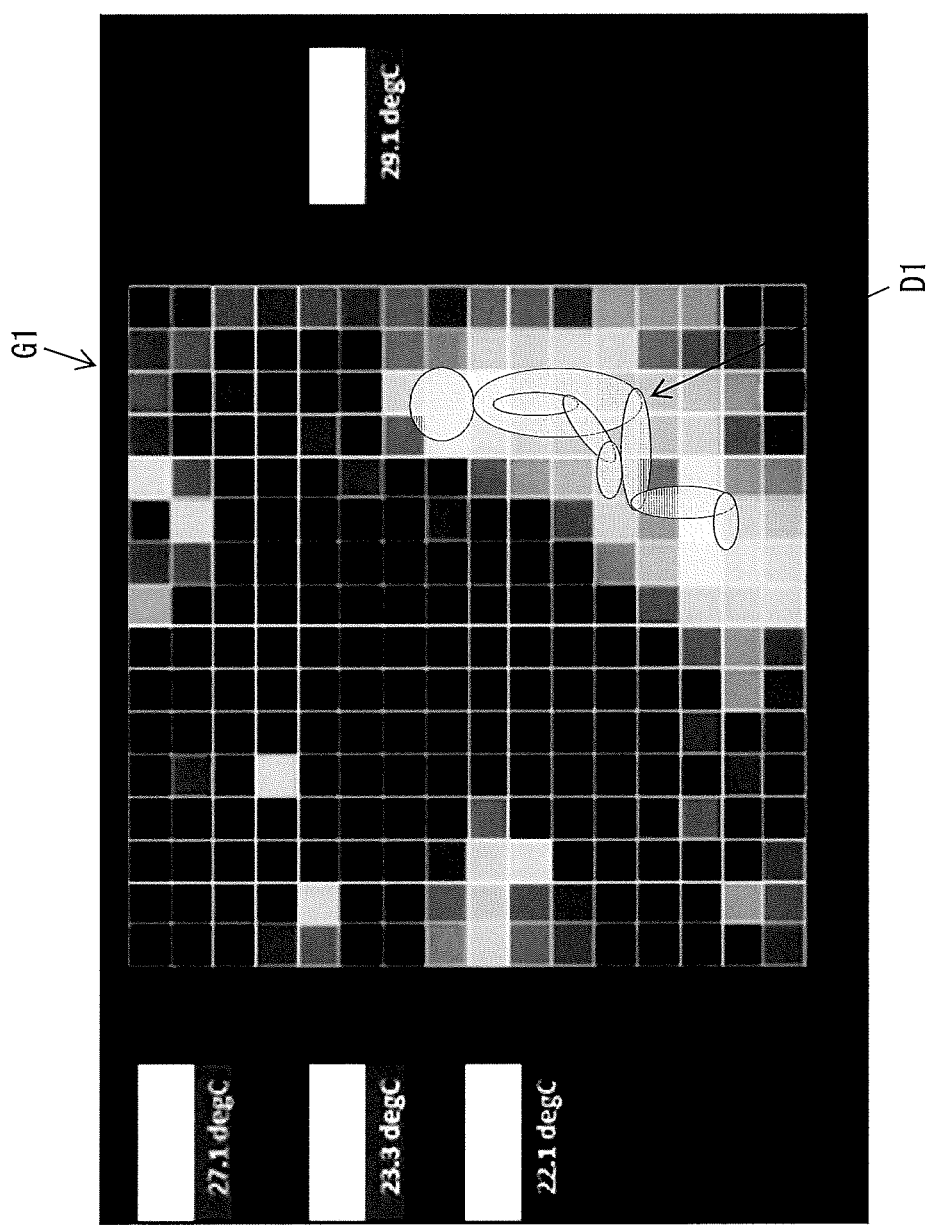
FIG. 12 shows an image displayed on the display device constituting the display control system in FIG. 1.

The display device 22 is, for example, a monitor of a host computer 22a installed in a nursing facility (see FIG. 4A), a mobile terminal 22b (see FIG. 4B), or the like, and displays an infrared image G1 obtained by imaging the care receiver P1 (see FIG. 12). The display device 22 is controlled by the display control device 10.

The host computer 22a is installed in a caregiver station in a nursing home, for example. This allows a caregiver to remotely check on a number of care receivers P1.

The portable terminal 22b encompasses a mobile phone, smart phone, tablet terminal, or the like owned by a caregiver.

Consequently, even if the caregiver is in the room of another care receiver P1, or is moving around somewhere, if an image is transmitted to the portable terminal 22b, in the event of an emergency the caregiver can rush straight to the care receiver P1.

2. Configuration of Display Control Device 10

As shown in FIG. 1, the display control device 10 in this embodiment comprises the image acquisition component 11, an orientation estimation component 12, a controller 13, a storage component 14, a determination component 15, and a count estimation component 16.

The image acquisition component 11 acquires from the infrared array sensors 21a and 21b the infrared image data captured by the infrared array sensors 21a and 21b.

The orientation estimation component 12 uses the infrared image data acquired by the image acquisition component 11 to estimate the orientation of the care receiver P1 in the room 30.

The orientation estimation done the orientation estimation component 12 is accomplished using a known method (see Patent Literature 1) involving a transition model (described below). The orientations of the care receiver P1 estimated by the orientation estimation component 12 include, for example, a standing position, a seated position, a supine position, a lateral recumbent position, a prone position, a half-sitting position, and so forth.

The controller 13 selects a dummy image (first dummy image) D1 (see FIG. 12) corresponding to each orientation stored in the storage component 14, on the basis of the orientation of the care receiver P1 estimated by the orientation estimation component 12. The selected dummy image D1 is then displayed on the display device 22 in a state of being superimposed over the infrared image G1.

Here, the dummy image D1 is an image showing a simplified view of the appearance and shape of the care receiver P1 whose orientation has been estimated, and images corresponding to a plurality of types of orientation are prepared. In this embodiment, dummy images D1 are prepared for the respective directions need to superimpose them over images of the care receiver P1 captured from above and from the side.

The display control of the display device 22 by the controller 13 will be described below in greater detail.

The storage component 14 stores the infrared image data acquired by the image acquisition component 11, in association with a plurality of dummy images D1 corresponding to a plurality of types of orientation of the care receiver P1 estimated by the orientation estimation component 12.

The dummy images D1 corresponding to the orientation of the care receiver P1 that are stored in the storage component 14 include, for example, a standing position, a seated position, a supine position, a lateral recumbent position, a prone position, and a half-sitting position.

These dummy images D1 are stored in the storage component 14 in a number of types corresponding to the orientations of the infrared image G1 in which the room 30 is imaged from above and the infrared image G1 as imaged from the side.

For example, with a standing position, a dummy image D1 to be superimposed over t the infrared image G1 captured from above, and a dummy image D1 to be superimposed over the infrared image G1 captured from the side may be provided. Similarly, with other orientations, dummy images D1 corresponding to the infrared image G1 from above and to the infrared image G1 from the side are stored in the storage component 14.

The determination component 15 determines how urgently the care receiver P1 in the room 30 needs care, on the basis of the infrared image data acquired by the image acquisition component 11.

More specifically, the determination component 15 refers, for example, to a plurality of infrared images G1 that have been acquired continuously (a moving picture), detects changes in flickering in the image, the expansion of a heat source, or the like, and thereby determines how urgently care is needed.

For instance, if the orientation of the care receiver P1 estimated by the orientation estimation component 12 is a seated position, and there is little change in flickering in the plurality of images continuously acquired by the image acquisition component 11, there is the risk that the care receiver P1 has slumped over while in a seated position.

Conversely, if the orientation of the care receiver P1 is a seated position, and there is a large amount of flicker in the plurality of images continuously acquired by the image acquisition component 11, it is presumed that the care receiver P1 is performing some operation, such as changing clothes or operating a portable terminal, while seated.

Thus, if there is almost no flickering over a long period while the same orientation is maintained in the plurality of infrared images G1 that are continuously acquired, the determination component 15 determines that there is an urgent need for care, and the controller 13 causes the display component 22 to give a warning display.

Figure 21B:
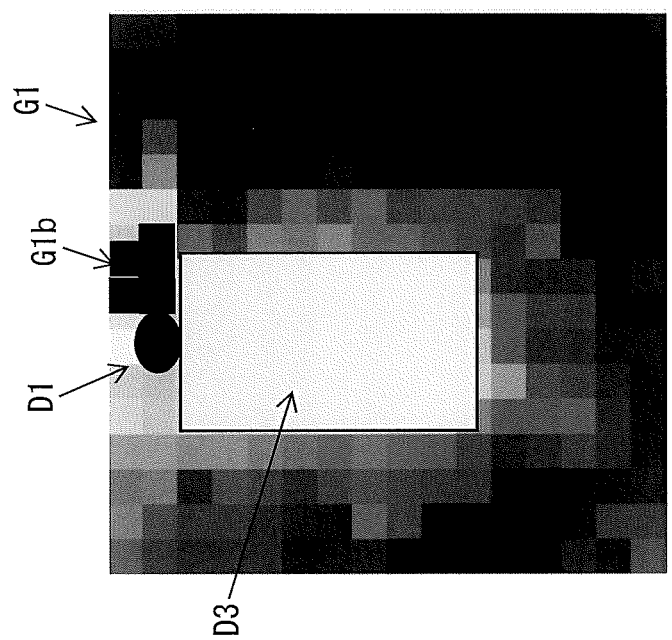
FIG. 21B is a diagram showing a recumbent image (heat source expansion around the head) captured using an infrared array sensor installed on the ceiling of the room shown in FIG. 2.

Also, if the orientation of the care receiver P1 estimated by the orientation estimation component 12 is a recumbent position, and a heat source in the plurality of images continuously acquired by the image acquisition component 11 has expanded, there is a high probability that the care receiver P1 is vomiting (see FIG. 21B).

Thus, in this case, the determination component 15 determines that there is an urgent need for care, and the controller 13 causes the display device 22 to give a warning display.

Here, examples of a warning display include flashing of the dummy image D1 on the display device 22, changing the color of the display, and giving a warning that combines text information. When the color is changed, for example, it may be changed from the normal display color of the dummy image D1 to red. Also, a warning display that combines text information may include, for example, a text display such as "care receiver needs nursing care!" A warning sound such as a beep may also be used in conjunction with the display.

The count estimation component 16 uses the infrared image data acquired by the image acquisition component 11 to estimate the number of people in the room 30.

More specifically, the count estimation component 16 senses a high-temperature portion presumed to be a human head included in the infrared image G1, and counts the number of such portions to estimate the number of people in the room 30.

The number of people estimated to be in the room 30 by the count estimation component 16 is sent to the controller 13. If the number of people in the room 30 estimated by the count estimation component 16 is two or more, the controller 13 performs no display control of the display device 22.

That is, with the display control device 10 in this embodiment, if the number of care receivers P1 residing in the room 30 is usually just one, for example, it is assumed that there is less need for watching over the room if there is someone in it other than the care receiver P1 (such as a caregiver, a close relative, or a friend).

Thus, with the display control apparatus 10 in this embodiment, when there is someone other than the care receiver P1 in the room 30, that is, when the value estimated by the count estimation component 16 is two or more, no display control is performed on the display device 22.

3. Display Control 3-1. Orientation Estimation

With the display control device 10 in this embodiment, as described above, the image acquisition component 11 acquires infrared image data captured by the infrared array sensors 21a and 21b. The orientation estimation component 12 then uses the infrared image G1 taken of the room 30 from above and the infrared image G1 taken from the side (both acquired by the image acquisition component 11) to estimate the orientation of the care receiver P1.

Estimation of the orientation of the care receiver P1 by the orientation estimation component 12 is performed by the following procedure.

That is, the orientation estimation component 12 performs orientation estimation by using examination information that includes region information representing an inspection region of the infrared image data (from above and from the side) at each orientation in a transition model of orientation of the human body, and reference value information representing a reference value for determining whether a transition has been made to each orientation.

The transition model information and examination information are used to estimate the orientation of the body at the current point in time.

Figures 5, 6:
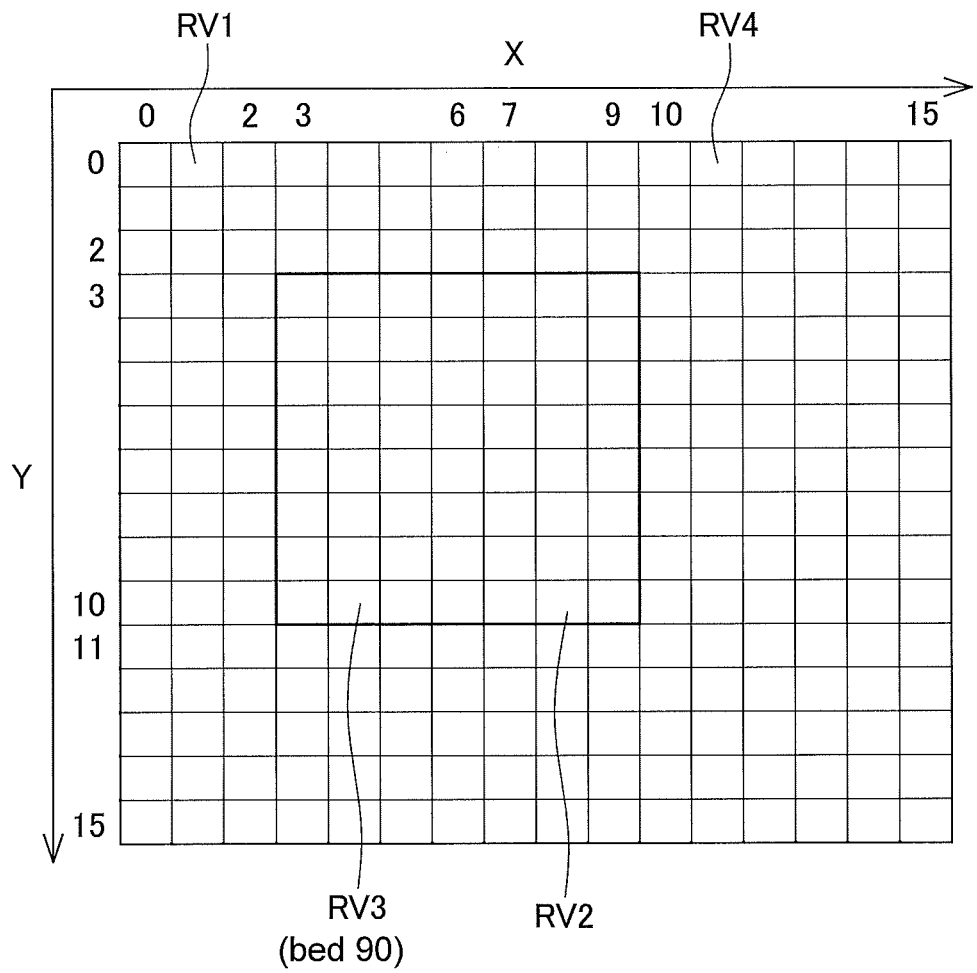
FIG. 5 is a diagram illustrating first image data used in orientation estimation by the orientation estimation component constituting the display control device in FIG. 1, and the examination region thereof.
FIG. 6 is a diagram illustrating second image data used in orientation estimation by the orientation estimation component constituting the display control device in FIG. 1, and the examination region thereof.

FIGS. 5 and 6 are diagrams illustrating the infrared image data captured from the ceiling 30a (from above) by the infrared array sensor 21a, and the examination region thereof. The infrared image data is made up of 16 pixels in the X direction and 16 pixels in the Y direction.

The region RV1 is the total region of the infrared image data, that is, a region in the range of $0 \leq X \leq 15$, $0 \leq Y \leq 15$.

The region RV2 is the region a specific width (3 pixels) from a position adjacent to the boundary in the lengthwise direction of the region corresponding to the bed 31 (see FIG. 2), that is, a region in the range of $7 \leq X \leq 9$, $3 \leq Y \leq 10$.

The region RV3 is the region corresponding to the bed 31, that is, a region in the range of $3 \leq X \leq 6$, $3 \leq Y \leq 10$.

The region RV4 is the region excluding the region RV3, and is made up of four regions. The first region is a region in the range of $0 \leq X \leq 2$, $0 \leq Y \leq 15$. The second region s a region in the range of $7 \leq X \leq 15$, $0 \leq Y \leq 15$. The third region is a region in the range of $3 \leq X \leq 6$, $0 \leq Y \leq 2$. The fourth region is a region in the range of $3 \leq X \leq 6$, $11 \leq Y \leq 15$.

Figures 7, 8:
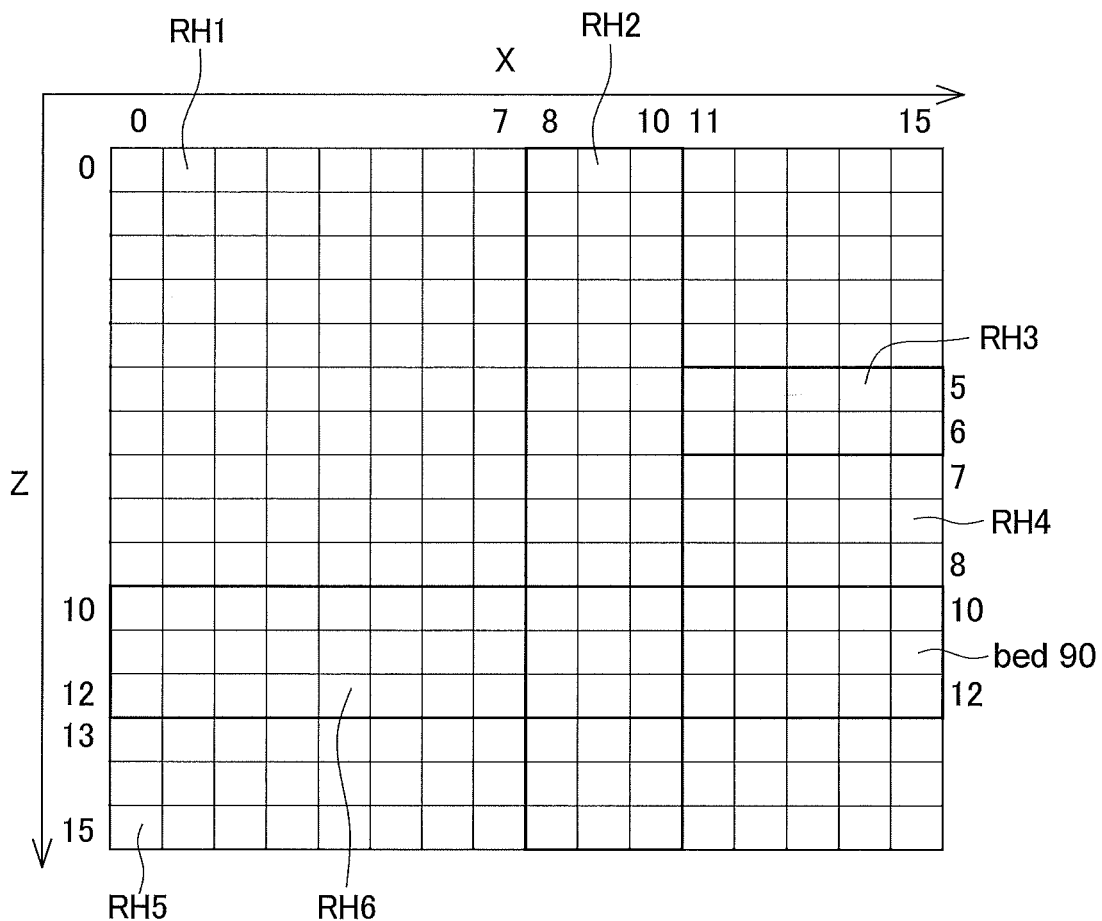
FIG. 7 is a diagram illustrating the examination regions of first and second image data used in orientation estimation by the orientation estimation component constituting the display control device in FIG. 1.
FIG. 8 is a diagram illustrating the examination regions of first and second image data used in orientation estimation by the orientation estimation component constituting the display control device in FIG. 1.

FIGS. 7 and 8 are diagrams illustrating the infrared image data taken from the wall 30b (from the side) by the infrared array sensor 21b, and the examination region thereof. The infrared image data is made up of 16 pixels in the X direction, and 16 pixels in the Z direction.

The region RH1 is the entire region of the second image data, that is, a region in the range of $0 \leq X \leq 15$, $0 \leq Z \leq 15$.

The range in the vertical direction (Z direction) of the region RH2 is the total range. The range in the horizontal direction (X direction) of the region RH2 is a range of a specific width (3 pixels) from a position adjacent to the range corresponding to the bed 31 ($11 \leq X \leq 15$). Therefore, the region RH2 is a region in the range of $8 \leq X \leq 10$, $0 \leq Z \leq 15$.

The range in the vertical direction (Z direction) of the region RH3 is a range of a specific width (5 pixels) from a position adjacent to the upper boundary of the range corresponding to the bed 31. The range in the horizontal direction (X direction) of the region RH3 is a range the same as the range corresponding to the bed 31. Therefore, the region RH3 is a region in the range of $11 \leq X \leq 15$, $5 \leq Z \leq 9$.

The range in the vertical direction (Z direction) of the region RH4 is a range of a specific width (three pixels) from a position adjacent to the upper boundary of the range corresponding to the bed 31. The range in the horizontal direction (X direction) of the region RH4 is a range the same as the range corresponding to the bed 31. Therefore, the region RH4 is a region in the range of $11 \leq X \leq 15$, $7 \leq Z \leq 9$.

The range in the horizontal direction of the region RH5 is a range obtained by excluding the range corresponding to the bed 31 from the entire range. The range in the vertical direction of the region RH5 is a range of a specific width (six pixels) upward from the lowest position (Z=15). Therefore, the region RH5 is a region in a range of $0 \leq X \leq 10$, $10 \leq Z \leq 15$.

The range in the horizontal direction of the region RH6 is a range obtained by excluding the range corresponding to the bed 31 from the entire range. The range in the vertical direction of the region RH6 is a range of a specific width (three pixels) upward from a specific position (Z=12). Therefore, the region RH6 is a region in a range of $0 \leq X \leq 10$, $10 \leq Z \leq 12$.

Figure 9:
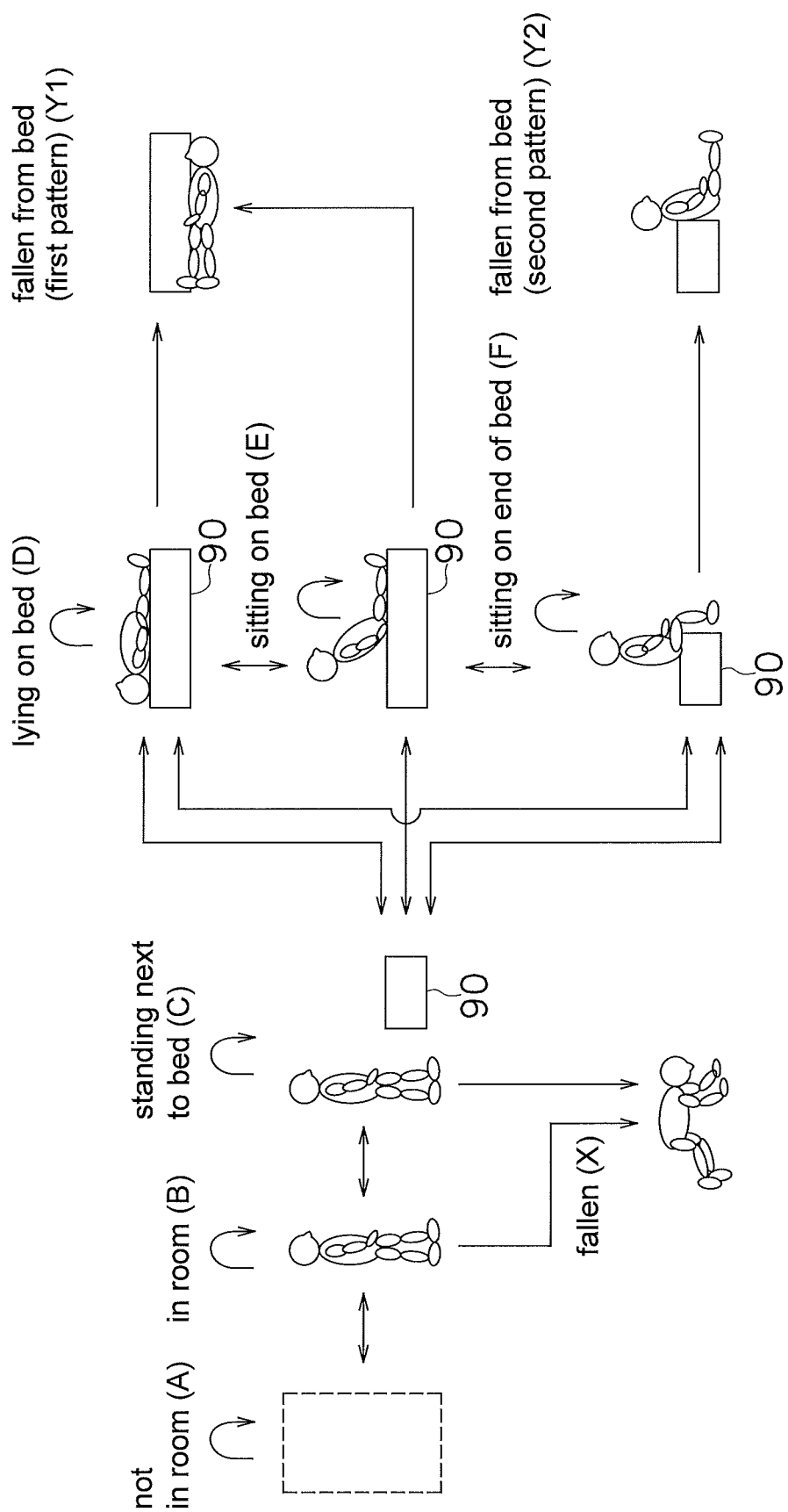
FIG. 9 is a diagram illustrating a transition model of orientation estimated by the orientation estimation component constituting the display control device in FIG. 1.

FIG. 9 is a diagram representing the transition model of the orientation of the care receiver (person) P1. FIG. 10 is a diagram representing transition model information.

The care receiver P1 (the person being monitored) is not in the room 30 in the initial state (A).

The orientation that comes after the orientation (A) is either that the person is in the room (B) or the original orientation (A).

The orientation that comes after the orientation (B) is either standing (C) next to the bed 31, fallen (X), not in the room (A), or the original orientation (B).

The orientation that comes after the orientation (C) is either lying on the bed 31 (D), sitting on the bed 31 (E), sitting on the end of the bed 31 (F), fallen (X), in the room (B), or the original orientation (C).

The orientation that comes after the orientation (D) is either sitting on the bed 31 (E), sitting in end of the bed 31 (F), standing next to the bed 31 (C), fallen from the bed 31 (first pattern) (Y1), or the original orientation (D).

The orientation that comes after the orientation (E) is either lying on the bed 31 (D), sitting on the end of the bed 31 (F), standing next to the bed 31 (C), fallen from the bed 31 (first pattern) (Y1), or the original orientation (E).

The orientation that comes after the orientation (F) is either lying on the bed 31 (D), sitting on the bed 31 (E), standing next to the bed 31 (C), fallen from the bed 31 (second pattern) (Y2), or the original orientation (F).

FIG. 11 is a table of region information representing the examination regions of the infrared image data for each of the orientations in the transition model, and reference value information representing reference values for determining whether there has been a transition to each orientation.

In order to determine whether or not there has been a transition to absence (A) in the room 30, the infrared array sensors 21a and 21b calculate the sum of the statistical quantity of the region RV1 of the infrared image data captured from above, plus the statistical quantity of the region RH1 of the infrared image data captured from the side. When this sum of the statistical quantities is at or above a reference value THA, it is determined that there has been a shift to the orientation (A).

In order to determine whether or not there has been a transition to being in the room 30 (B), the infrared array sensors 21a and 21b calculate the sum of the statistical quantity of the region RV1 of the infrared image data captured from above, plus the statistical quantity of the region RH1 of the infrared image data captured from the side. When this sum of the statistical quantities is at or above a reference value THB, it is determined that there has been a shift to the orientation (B).

In order to determine whether or not there has been a transition to standing next to the bed 31 (C), the infrared array sensors 21a and 21b calculate the sum of the statistical quantity of the region RV2 of the infrared image data captured from above, plus the statistical quantity of the region RH2 of the infrared image data captured from the side. When this sum of the statistical quantities is at or above a reference value THC, it is determined that there has been a shift to the orientation (C).

In order to determine whether or not there has been a transition to lying on the bed 31 (D), the infrared array sensors 21a and 21b calculate the sum of the statistical quantity of the region RV3 of the infrared image data captured from above, plus the statistical quantity of the region RH4 of the infrared image data captured from the side. When this sum of the statistical quantities is at or above a reference value THD, it is determined that there has been a shift to the orientation (D).

In order to determine whether or not there has been a transition to sitting on the bed 31 (E), the infrared array sensors 21a and 21b calculate the sum of the statistical quantity of the region RV3 of the infrared image data captured from above, plus the statistical quantity of the region RH3 of the infrared image data captured from the side. When this sum of the statistical quantities is at or above a reference value THE, it is determined that there has been a shift to the orientation (E).

In order to determine whether or not there has been a transition to sitting on the end of the bed 31 (F), the infrared array sensors 21a and 21b calculate the sum of the statistical quantity of the region RV3 of the infrared image data captured from above, plus the statistical quantity of the region RH2 of the infrared image data captured from the side. When this sum of the statistical quantities is at or above a reference value THF, it is determined that there has been a shift to the orientation (F).

In order to determine whether or not there has been a transition to having fallen (X), the infrared array sensors 21a and 21b calculate the sum of the statistical quantity of the region RV4 of the infrared image data captured from above, plus the statistical quantity of the region RH5 of the infrared image data captured from the side. When this sum of the statistical quantities is at or above a reference value THX, it is determined that there has been a shift to the orientation (X).

Here, in order to determine whether or not there has been a transition to having fallen from the bed 31 (first pattern) (Y1), the infrared array sensors 21a and 21b calculate the sum of the statistical quantity of the region RV2 of the infrared image data captured from above, plus the statistical quantity of the region RH6 of the infrared image data captured from the side. When this sum of the statistical quantities is at or above a reference value THY1, it is determined that there has been a shift to the orientation (Y1).

The reason why the region RH6 is used for this determination is that the location where the infrared array sensor 21b is installed is only a short distance from the location where the care receiver P1 has fallen out of the bed 31, so with the infrared image data captured from the side, the captured portion of the care receiver P1 who has fallen is at a position higher than the lowest line (Y=15).

Also, in order to determine whether or not there has been a transition to having fallen from the bed 31 (second pattern) (Y2), the infrared array sensors 21a and 21b calculate the sum of the statistical quantity of the region RV2 of the infrared image data captured from above, plus the statistical quantity of the region RH6 of the infrared image data captured from the side. When this sum of the statistical quantities is at or above a reference value THY2, it is determined that there has been a shift to the orientation (Y2).

The reason why the region RH6 is used for this determination is the same as with falling out of the bed 31 (first pattern).

3-2. Display Control

With the display control device 10 in this embodiment, as a result of the above-mentioned orientation estimation, the display device 22 is controlled so that the dummy image D1 corresponding to each orientation stored in the storage component 14 is displayed superimposed over the infrared image G1 on the basis of the estimated orientation of the care receiver P1.

That is, the storage component 14 stores a plurality of the dummy images D1 corresponding to the orientations of the care receiver P1 estimated by the orientation estimation component 12. Therefore, as shown in FIG. 12, the controller 13 checks the result of the attitude estimation by the orientation estimation component 12, reads the appropriate dummy image D1 corresponding orientation of the care receiver P1 in the infrared image G1 from the storage component 14, and displays this image superimposed over the thermal image G1.

Here, when the dummy image D1 corresponding to the estimated orientation is displayed superimposed over the infrared images G1, the superposition is based on the position of the head of the care receiver P1.

More precisely, in the infrared image G1, the head and face portions are usually located higher up on the body, and are usually exposed most of the time, so these portions are represented as having a higher temperature. Thus, the head and face portions of the dummy image D1 are positioned so as to be superimposed in their display on the display device 22, based on the estimated position of the heat and face portions in the infrared image G1.

3-3. Flow of Display Control

Figure 13:
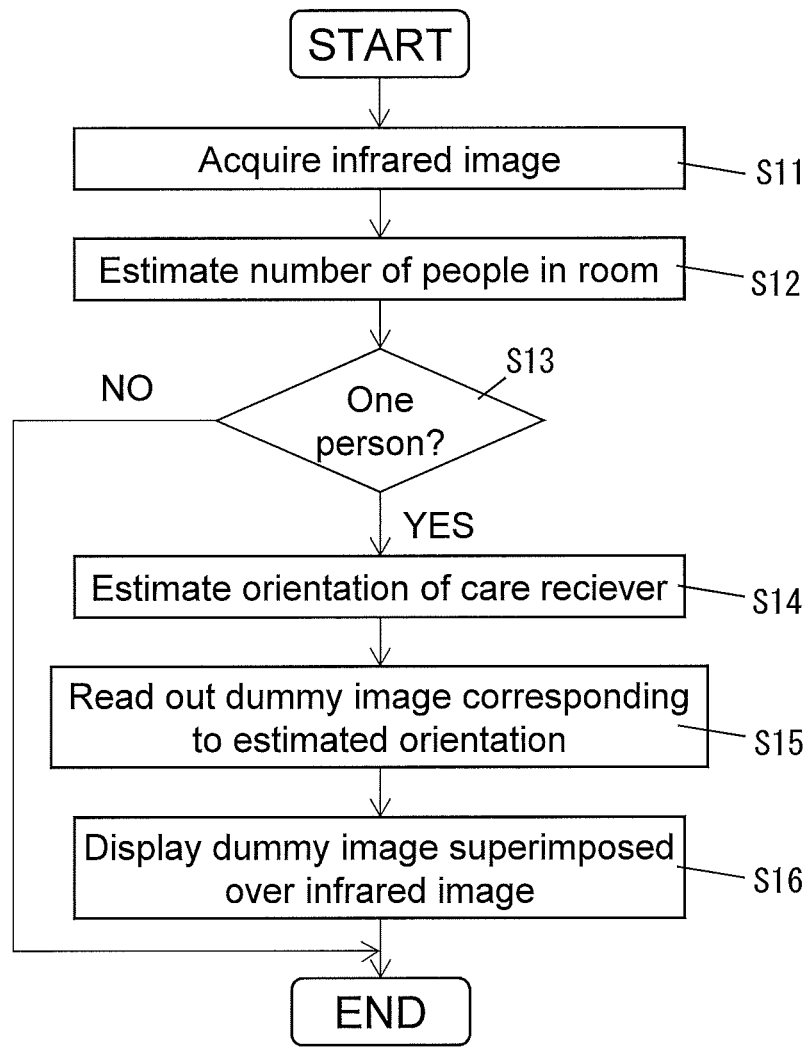
FIG. 13 is a flowchart showing the flow of display control by the display control device in FIG. 1.

The display control device 10 in this embodiment carries out display control according to the flowchart shown in FIG. 13.

That is, in step S11, the image acquisition component 11 acquires the infrared image G1 captured in the room 30 from above and from the side, using the two infrared array sensors 21a and 21b.

Next, in step S12, the count estimation component 16 uses the infrared image G1 thus acquired to estimate the number of people in the room 30.

Next, in step S13, it is determined whether or not the number of people in the room 30 estimated by the count estimation component 16 just one. If there is only one person, the process proceeds to step S14. On the other hand, if there are two or more people, it is determined that someone other than the care receiver P1 is in the room 30 and can provide care, and the display control process is ended.

Next, in step S14, the orientation estimation component 12 estimates the orientation of the care receiver P1 determined to be the only person in the room 30 in step S13.

Next, in step S15, the controller 13 reads from the storage component 14 the dummy image D1 corresponding to the orientation (such as a standing position) of the care receiver P1 estimated in step S14.

Next, in step S16, the controller 13 superimposes and displays the dummy image D1 read out from the storage component 14, based on the head or face portion of the care receiver P1 included in the infrared image G1.

Consequently, the caregiver can recognize the orientation of the care receiver P1 displayed on the display device 22, and can easily determine whether or not there is any abnormality.

3-4. Flow of Orientation Estimation

Figure 14:
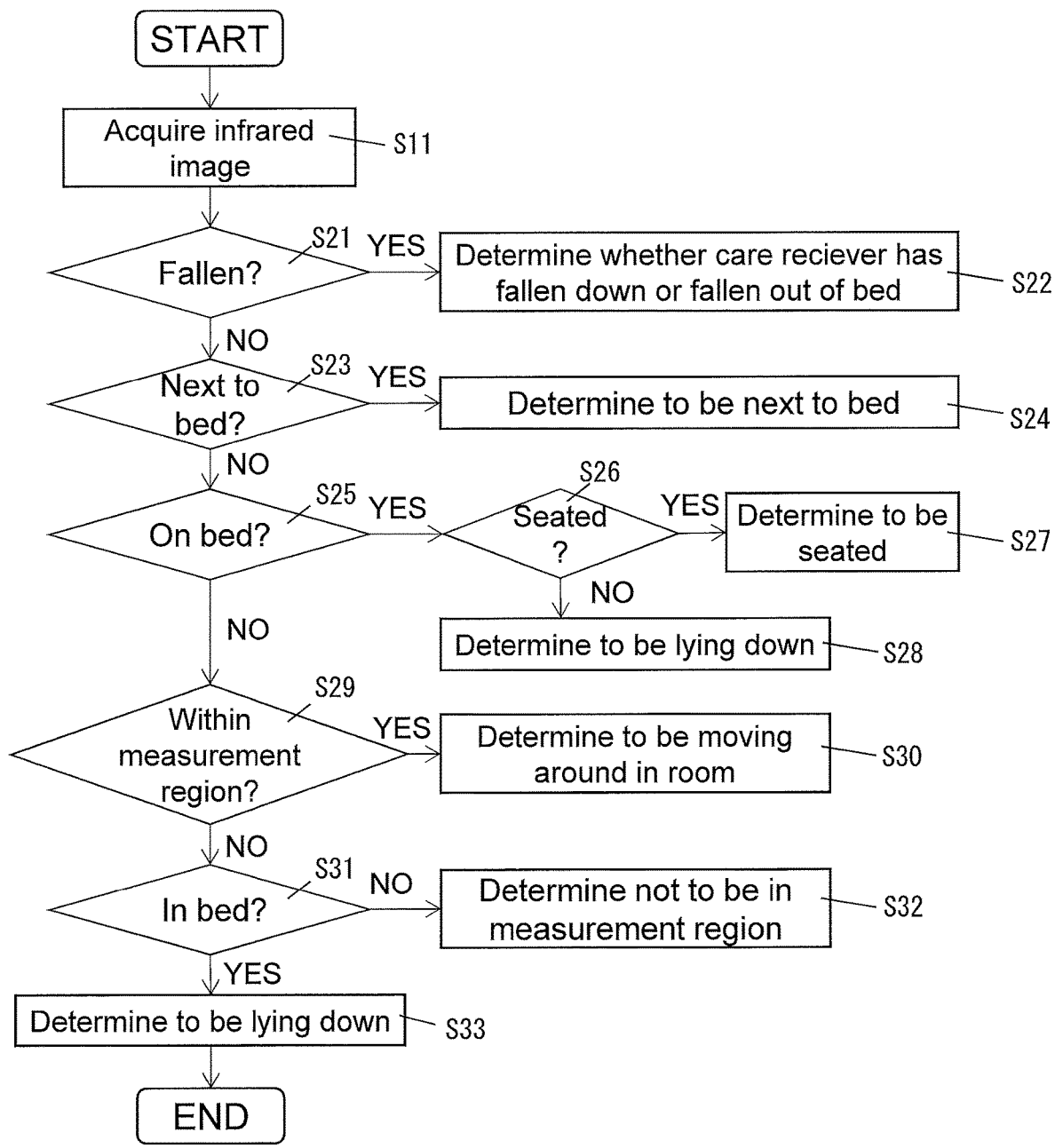
FIG. 14 is a flowchart showing the flow of orientation estimation by the display control device in FIG. 1.

With the display control device 10 in this embodiment, the orientation estimation in step S14 in the flowchart of FIG. 13 is carried out according to the flowchart shown in FIG. 14.

That is, after the infrared image G1 is acquired from the infrared array sensors 21a and 21b in step S11, it is determined in step S21 whether or not the orientation of the care receiver P1 in the infrared image G1 is indicates that the person has fallen down. Here, if it is determined that the person has fallen down, the process proceeds to step S22. On the other hand, if it is determined that the person has not fallen down, that means the orientation is something other than having fallen down, so the process proceeds to step S23.

Next, in step S22, the orientation estimation component 12 determines that the care receiver P1 is in a fallen orientation based on the determination result in step S21.

Next, in step S23, it is determined whether or not the care receiver P1 is at the side of the bed in the infrared image G1. Here, if the care receiver P1 is determined to be at the side of the bed, the process proceeds to step S24. On the other hand, if the care receiver P1 has been determined not to be at the side of the bed, the process proceeds to step S25.

Next, in step S24, it is determined from the result of determination by the orientation estimation component 12 in step S23 that there is someone next to the bed.

Next, in step S25, it is determined whether or not the care receiver P1 in the infrared image G1 is on the bed. If it is determined that the care receiver P1 is on the bed, the process proceeds to step S26. On the other hand, if it is determined that the care receiver P1 is not on the bed, the process proceeds to step S29.

Next, in step S26, it is determined whether or not the care receiver P1 in the infrared images G1 is in a seated position on the bed. Here, if it has been determined that the care receiver P1 is in a seated position on the bed, the process proceeds to step S27. On the other hand, if the care receiver P1 has been determined not to be in a seated position on the bed, the process proceeds to step S28.

Next, in step S27, it is determined from the result of determination by the orientation estimation component 12 in step S26 that the care receiver P1 is in a seated position on the bed.

Next, in step S28, it is determined from the result of determination by the orientation estimation component 12 in step S26 that the care receiver P1 is in a recumbent position on the bed.

Next, in step S29, since the care receiver P1 is neither the beside the bed or on the bed, it is determined whether or not the care receiver P1 is within the measurement region in the infrared image G1. Here, if it is determined that the care receiver P1 is within the measurement region, the process proceeds to step S30. On the other hand, if it is determined that the care receiver P1 is outside the measurement region, the process proceeds to step S31.

Next, in step S30, it is determined that the care receiver P1 is moving somewhere within the room 30 other than next to the bed or on the bed.

Next, in step S31, it is checked once again whether the care receiver P1 is on the bed. Here, if it is determined that the care receiver P1 is on the bed, the process proceeds to step S33. On the other hand, if the person is determined not to be on the bed, the process proceeds to step S32.

Next, in step S32, it is determined from the result of determination using the infrared image G1 that the care receiver P1 has not fallen down and is not within the measurement region next to the bed or on the bed, and is therefore outside the measurement region.

Next, in step S33, since it has been determined in step S32 that the care receiver P1 is on the bed, it is determined that the person is in a recumbent position covered by a blanket, for example.

4. Display Example of Dummy Image for Each Orientation 4-1. Standing Position

Figure 15B:
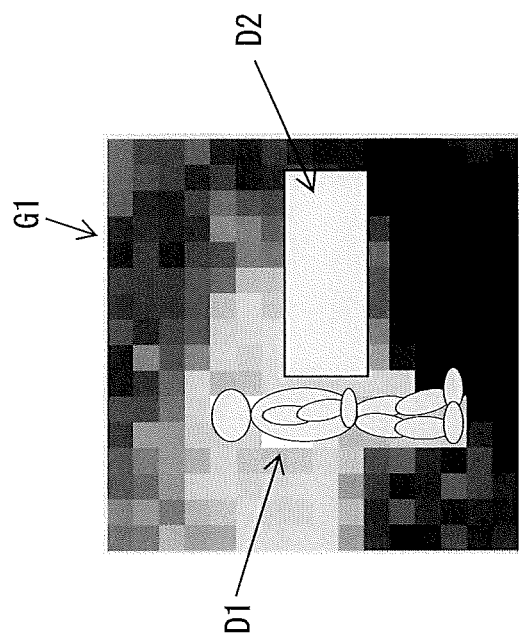
FIGS. 15A and 15B show a standing image captured using two infrared array sensors (on the ceiling and to the side) installed in the room shown in FIG. 2.
Figure 15A:
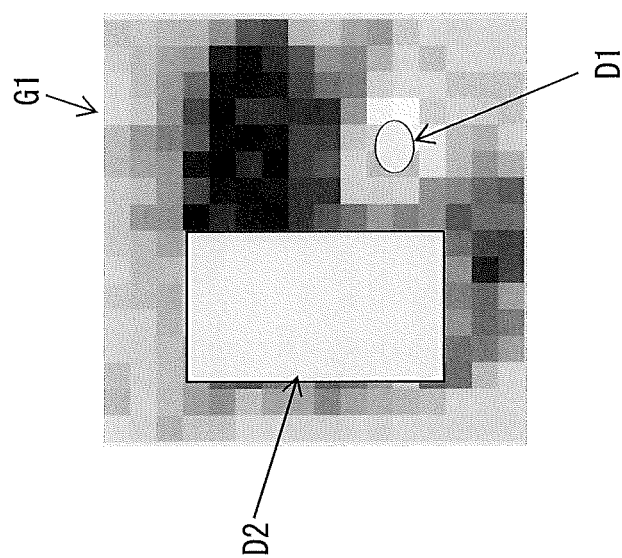

As shown in FIGS. 15A and 15B when the care receiver P1 is in a standing position, a dummy image D1 showing a state in which the care receiver P1 is standing is displayed superimposed over the infrared image G1.

More specifically, as shown in FIG. 15A, in the infrared image G1 acquired from the infrared array sensor 21a, which captures an image of the room 30 from above, the care receiver P1 is imaged from above his head, so a dummy image D1 is used in which the head and shoulder portions are displayed in plan view.

On the other hand, as shown in FIG. 15B, in the infrared image G1 acquired from the infrared array sensor 21b, which captures an image of the room 30 from the side, the care receiver P1 is imaged from his side, so a dummy image D1 (second dummy image) is used in which the entire body of the care receiver P1 is displayed.

A dummy image (second dummy image) D2 showing the bed 31 as a piece of interior furnishing is displayed on the infrared image G1 shown in FIGS. 15A and 15B.

Consequently, where the care receiver P1 is located within the room 30 can be recognized while referring to the position of the bed 31 or other such interior furnishings.

4-2. Seated Position

As shown in FIGS. 16A and 16B, if the care receiver P1 is in a seated position, a dummy image D1 showing a state in which the care receiver P1 is sitting in a wheelchair or a chair is displayed superimposed over the infrared image G1.

More specifically, as shown in FIG. 16A, in the infrared image G1 acquired from the infrared array sensor 21a that images the room 30 from above, the care receiver P1 is imaged from above his head, so a dummy image D1 is used in which the legs are displayed in plan view in addition to the head and shoulder portions.

On the other hand, as shown in FIG. 16B, in the infrared image G1 acquired from the infrared array sensor 21b that images the room 30 from the side, the care receiver P1 is imaged from above his side, so a dummy image D1 is used in which the care receiver P1 is bent at the waist.

4-3. Recumbent Position (with Blanket)

Figure 17A:
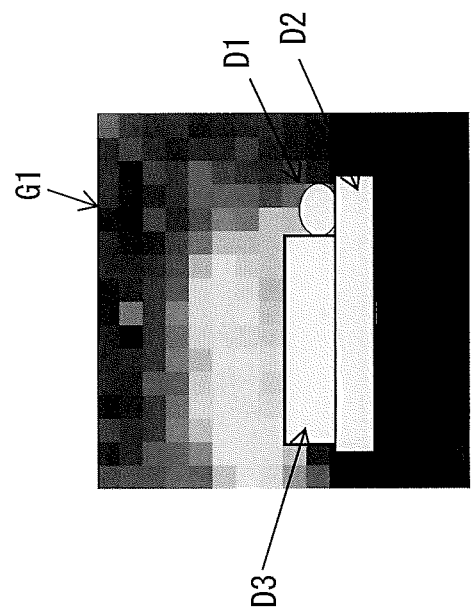
FIGS. 17A and 17B show a recumbent image (with a blanket) captured using two infrared array sensors (on the ceiling and to the side) installed in the room shown in FIG. 2.
Figure 17B:
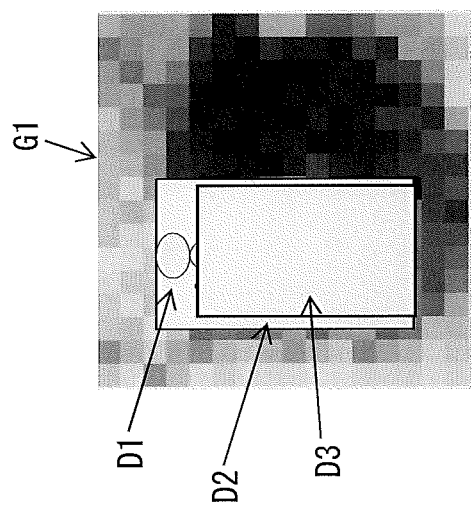

As shown in FIGS. 17A and 17B, if the care receiver P1 is in a recumbent position in which he is sleeping on the bed 31, a dummy image D1 showing a state in which the care receiver P1 is lying on the bed 31 the shown is displayed superimposed over the infrared image G1.

More specifically, as shown in FIG. 17A, in the infrared image G1 acquired from the infrared array sensor 21a that images the room 30 from above, the sleeping care receiver P1 is imaged from above, so a dummy image D1 is used in which the entire body of the care receiver P1 is displayed.

If the care receiver P1 sleeping on the bed 31 is covered by a blanket (dummy image D3), as shown in FIG. 17A, the portion that is covered by the blanket in the infrared image G1 is displayed as a portion of lower temperature, and just the head is displayed as a portion of higher temperature.

Meanwhile, as shown in FIG. 17B, in the infrared image G1 acquired from the infrared array sensor 21b that images the room 30 from the side, the care receiver P1 is imaged from the side, so a dummy image D1 is used in which the care receiver P1 is displayed in a recumbent position in which he is sleeping on the bed 31.

Similarly to FIG. 17A, if the care receiver P1 sleeping on the bed 31 is covered with a blanket, as shown in FIG. 17B, in the infrared image G1 the portion covered with the blanket is displayed as a portion of lower temperature, and just the head is displayed as a portion of higher temperature.

4-4. Recumbent Position (Blanket Turned Down)

Figure 18B:
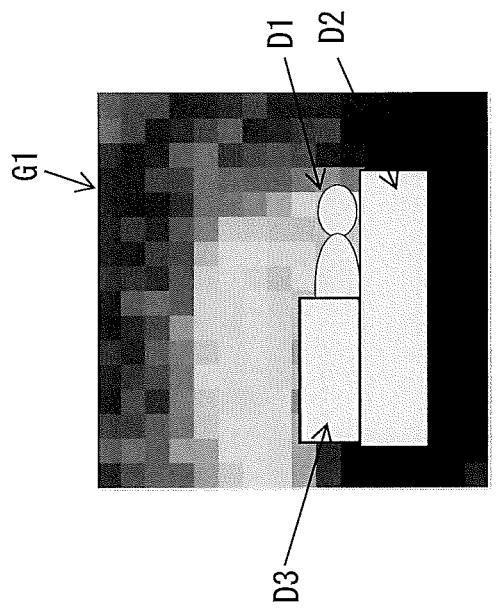
FIGS. 18A and 18B show a recumbent image (with the blanket turned down) captured using two infrared array sensors (on the ceiling and to the side) installed in the room shown in FIG. 2.
Figure 18A:
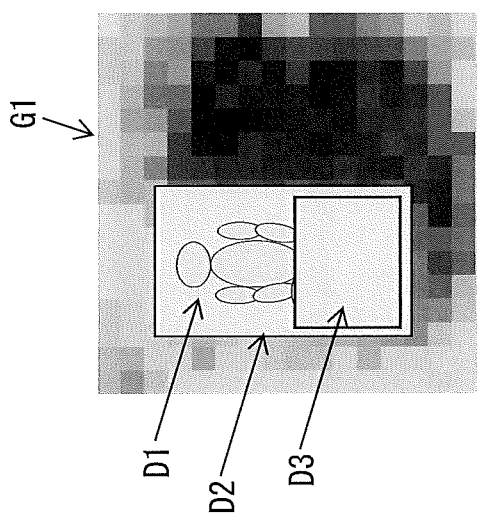

As shown in FIGS. 18A and 18B, if the care receiver P1 is in a recumbent position in which he is sleeping on the bed 31 and has the blanket (dummy image D3) turned down, a dummy image D1 showing a state in which the care receiver P1 is sleeping on the bed 31 is displayed superimposed over the infrared image G1.

More specifically, as shown in FIG. 18A, in the infrared image G1 acquired from the infrared array sensor 21a that images the room 30 from above, the sleeping care receiver P1 is imaged from above, so a dummy image D1 is used in which the upper half of the body of the care receiver P1 is displayed.

If the lower half of the body of the care receiver P1 sleeping on the bed 31 is covered by a blanket (dummy image D3), as shown in FIG. 18A, in the infrared image G1 the portion covered by a blanket is displayed as a portion of lower temperature, and just the upper half of the body is displayed as a portion of higher temperature.

On the other hand, as shown in FIG. 18B, in the infrared image G1 acquired from the infrared array sensor 21b that images the room 30 from the side, the care receiver P1 is imaged from the side, so a dummy image D1 is used in which the care receiver P1 is displayed in a recumbent position in which he is sleeping on the bed 31.

Similarly to FIG. 18A, if the lower half of the body of the care receiver P1 sleeping on the bed 31 is covered by a blanket, as shown in FIG. 18B, in the infrared image G1 the portion covered with the blanket is displayed as a portion of lower temperature, and just the upper half of the body is displayed as a portion of higher temperature.

4-5. Recumbent Position (Fallen)

As shown in FIGS. 19A and 19B, if the care receiver P1 is in a recumbent position in which he has fallen next to the bed 31, a dummy image D1 showing a state in which the care receiver P1 has fallen next to the bed 31 (dummy image D2) is displayed superimposed over the infrared image G1.

More specifically, as shown in FIG. 19A, in the infrared image G1 acquired from the infrared array sensor 21a that images the room 30 from above, the care receiver P1 lying next to the bed 31 is imaged from above, so a dummy image D1 is used in which the entire body of the care receiver P1 is displayed.

In this case, the care receiver P1 is sleeping in a different location from that in the dummy image D2 showing the bed 31, and is assumed to have fallen, so the dummy image D1 is, for example, shown in red, yellow, or some other color that is different from the normal color, or is flashing.

On the other hand, as shown in FIG. 19B, in the infrared image G1 acquired from the infrared array sensor 21b that images the room 30 from the side, the care receiver P1 is imaged from the side, so a dummy image D1 is used in which the care receiver P1 is displayed in a recumbent position in which he is sleeping below the bed 31.

Similarly to FIG. 19A, if the care receiver P1 is sleeping below the bed 31, it is assumed that he has fallen, so the dummy image D1 is, for example, shown in red, yellow, or some other color that is different from the normal color, or is flashing.

This allows a caregiver to check the infrared image G1 shown in FIGS. 19A and 19B and recognize a state in which care is urgently required.

4-6. Seated Position (Fallen)

Figure 20B:
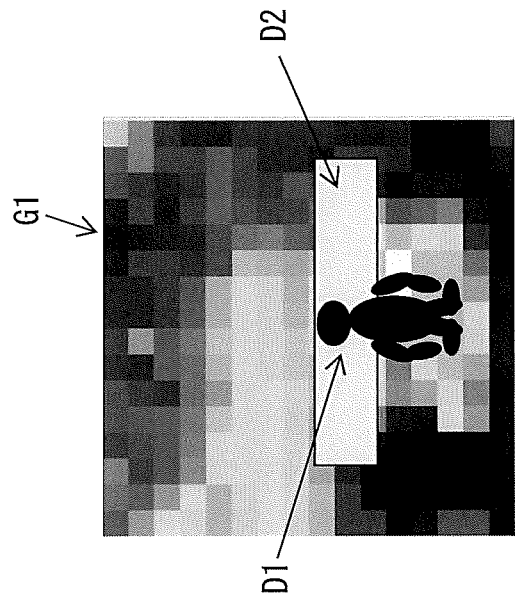
FIGS. 20A and 20B show a rolled-over seated image (emergency) captured using two infrared array sensors (on the ceiling and to the side) installed in the room shown in FIG. 2.
Figure 20A:
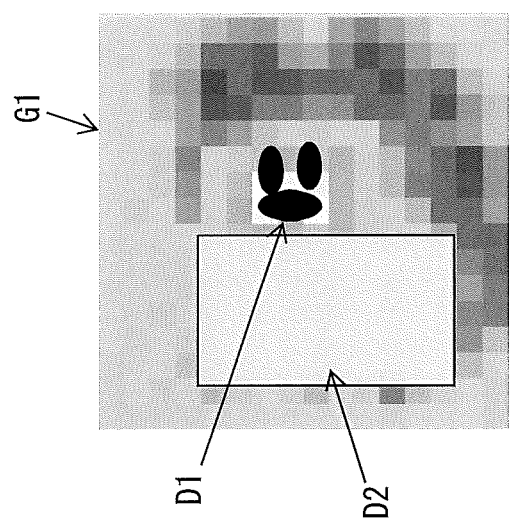

As shown in FIGS. 20A and 20B, when the care receiver P1 is in a seated position next to the bed 31, a dummy image D1 showing a state in which the care receiver P1 has fallen and is slumped over next to the bed 31 (dummy image D2) is displayed superimposed over the infrared image G1.

More specifically, as shown in FIG. 20A, in the infrared image G1 acquired from the infrared array sensor 21a that images the room 30 from above, the care receiver P1 who is sitting next to the bed is imaged from above, so a dummy image D1 is used in which the head, shoulders, and lefts of the care receiver P1 are displayed in plan view.

In this case, since the care receiver P1 is assumed to have fallen away from the dummy image D2 showing the bed 31 and is sitting next to it, the dummy image D1 is, for example, shown in red, yellow, or some other color that is different from the normal color, or is flashing.

On the other hand, as shown in FIG. 20B, in the infrared image G1 acquired from the infrared array sensor 21b that images the room 30 from the side, the care receiver P1 is imaged from the side, so a dummy image D1 is used in which the care receiver P1 is displayed in a seated position in which he is sitting and slumped against the bed 31.

Similarly to FIG. 20A, if the order care receiver P1 is sitting next to the bed 31, it is assumed that he has fallen and is slumped over, so the dummy image D1 is, for example, shown in red, yellow, or some other color that is different from the normal color, or is flashing.

This allows a caregiver to check the infrared image G1 shown in FIGS. 20A and 20B and recognize a state in which care is urgently required.

The urgency of a care receiver P1 who is in a seated position next to the bed 31 can be determined by checking a continuously acquired infrared image G1 and looking for any movement.

4-7. Recumbent Position (with Flickering)

Figure 21A:
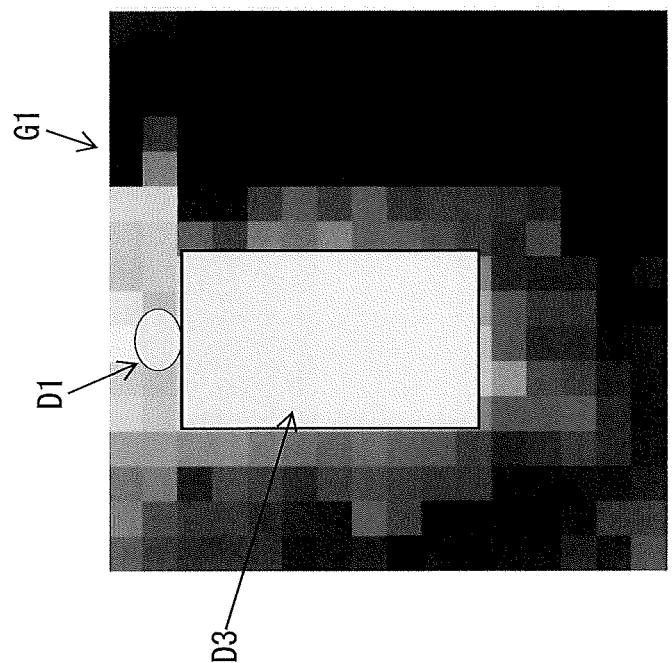
FIG. 21A is a diagram showing a recumbent image (no flickering) captured using an infrared array sensor installed on the ceiling of the room shown in FIG. 2.

As shown in FIG. 21A, when the care receiver P1 is a recumbent position and there is little flickering in the continuously acquired infrared image, there is a high probability that the care receiver P1 is asleep.

Thus, in this case, the determination component 15 determines that this is not a state in which the care receiver P1 needs care.

As shown in FIG. 22A, when the care receiver P1 is a recumbent position and a flicker region G1a with a large amount of flickering is detected in the continuously acquired infrared image near the upper half of the body of the care receiver P1, there is a high probability that the care receiver P1 is trying to get up.

Furthermore, as shown in FIG. 22B, when the care receiver P1 is a recumbent position and a flicker region G1a with a large amount of flickering is detected in the continuously acquired infrared image near the upper half of the body of the care receiver P1 who is covered with a blanket, there is a high probability that the care receiver P1 is trying to get up.

In this case, the care receiver P1 needs help getting up, so the determination component 15 determines this to be a state in which care is required.

Here, determination using the flickering of pixels in the infrared image G1 is carried out as follows.

That is, in performing determination based on the flickering of a continuously acquired infrared image, the determination component 15 makes its determination according to the fluctuation of the position of the thermal center of gravity in the image.

More specifically, the position of the thermal center of gravity is found, for example, by cutting out a region in which the temperature is at least a specific amount above room temperature from the infrared image G1, and finding the average position in the XY direction of the pixels of the cut-out region. The position of this thermal center of gravity may be determined as a measure of how urgently care is needed, according to whether or not the position has moved (fluctuated) from a specific threshold.

Consequently, when an infrared sensor is used as the image sensor, the characteristics of an infrared image (a thermal image) can be utilized to determine a state in which the care receiver P1 needs care when the change in the position of the thermal center of gravity is smaller than a predetermined threshold, for example.

Conversely, if the change in the position of the thermal center of gravity is greater than a predetermined threshold, it can be determined, for example, that the care receiver is changing clothes, operating a portable terminal, or in some other such state that does not require care.

As a result, the caregiver can look at the image of the care receiver P1 displayed on the display component 22 and accurately determine whether or not care is needed.

4-8. Recumbent Position (Heat Source Expansion)

As shown in FIG. 21B, when the care receiver P1 is a recumbent position and a heat source expansion region G1b is detected in which a heat source near the head is expanding in the continuously acquired infrared image, there is a high probability that the care receiver P1 has vomited while sleeping.

Therefore, in this case, the determination component 15 determines that this is a state in which the care receiver P1 needs care urgently.

The controller 13 takes into account the result of estimating the orientation by the orientation estimation component 12 and the result of determining the urgency of care by the determination component 15, and controls the display so that the dummy image D1 is changed to another color, is flashed, etc., as shown in FIG. 21B.

This allows the caregiver to check the screen displayed on the display device 22 and easily recognize that the care receiver P1 is a recumbent position and urgently needs care.

4-9. Seated Position (with Flickering)

Figure 23:
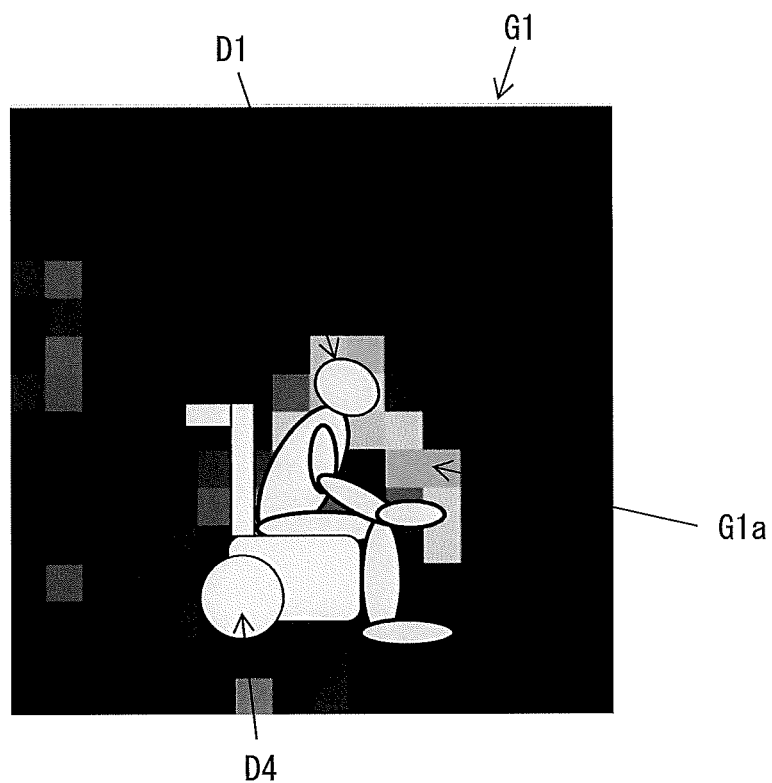
FIG. 23 shows a seated image (vigorous flickering) captured using an infrared array sensor installed on a side wall of the room shown in FIG. 2.

As shown in FIG. 23, when the care receiver P1 is in a seated position in a dummy image D4 of a wheelchair (second dummy image), if a flicker region G1a is detected in which there is a large amount of flickering near the upper half of the body of the care receiver P1 on the dummy image D4 showing the wheelchair 32 in the continuously acquired infrared image, there is a high probability that care receiver P1 is changing clothes.

Thus, in this case, the determination component 15 determines that this is not a state in which the care receiver P1 needs care.

Conversely, when the care receiver P1 is in a seated position in the wheelchair 32 and there is almost no flickering for at least a certain length of time near the upper half of the body of the care receiver P1 in the continuously acquired infrared image, there is the risk that the care receiver P1 is slumped over in the wheelchair.

Thus, in this case, the determination component 15 determines that this is a state in which the care receiver P1 needs care.

In this case, the controller 13 takes into account the result of estimating the orientation by the orientation estimation component 12 and the result of determining the urgency of care by the determination component 15, and controls the display so that the dummy image D1 is changed to another color, is flashed, etc.

Consequently, the caregiver can recognize that the care receiver P1 has been stationary in the wheelchair for a long time, and can rush to the room of the care receiver P1.

Other Embodiments

An embodiment of the present invention was described above, but the present invention is not limited to or by the above embodiment, and various modifications are possible without departing from the gist of the invention.

(A)

In the above embodiment, an example was given in which the present invention was implemented as the display control device 10 for conducting the above-mentioned display control method, and as the display control system 20 comprising said device, but the present invention is not limited thereto.

For instance, the present invention may be implemented as the above-mentioned display control method.

Alternatively, the present invention may be implemented as a display control program for causing a computer to execute the above-mentioned display control method. Furthermore, the present invention may be implemented as a non-transitory computer-readable storage medium for storing this display control program.

Regardless of how the invention is implemented, it allows the same effect as described above to be obtained.

(B)

In the above embodiment, as shown in FIG. 1, the display control device 10 comprising the storage component 14 for storing dummy images D1 corresponding to various orientations of the care receiver P1 was described as an example, but the present invention is not limited thereto.

Figure 24:
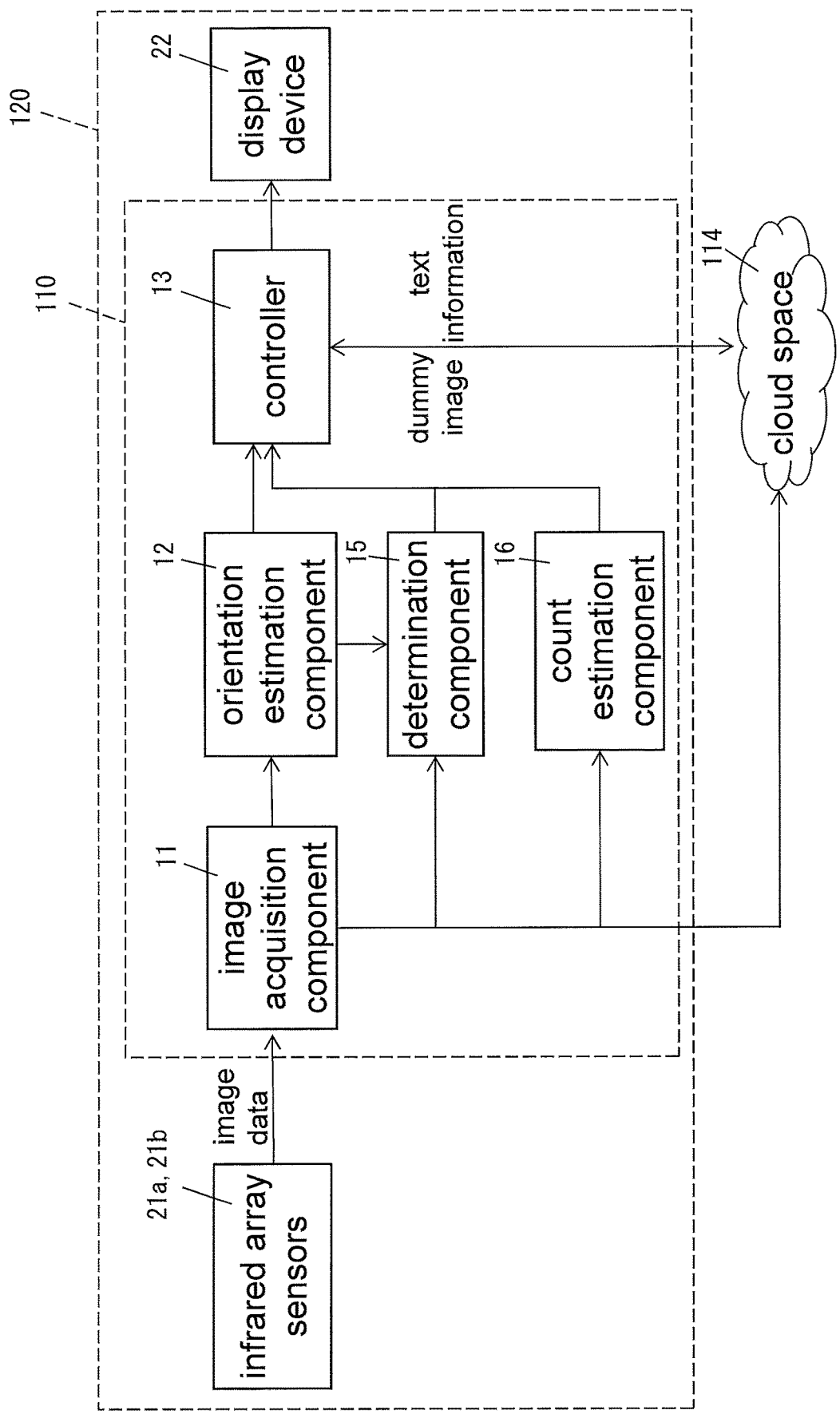
FIG. 24 is a block diagram of the configuration of a display control device according to another embodiment of the present invention, and a display control system comprising this device.

For example, as shown in FIG. 24, a cloud space 114 provided outside the display control device 110 and the display control system 120, or the like, may be used as a storage component for storing the dummy images.

That is, the display control device of the present invention may be configured not to have an internal storage component, so long as the configuration is one in which dummy images are read from an external storage component (cloud space, server, etc.).

(C)

In the above embodiment, an example was described in which the dummy image D1 was displayed superimposed over the infrared image G1 on the display device 22, but the present invention is not limited to this.

Figures 25A, 25B:
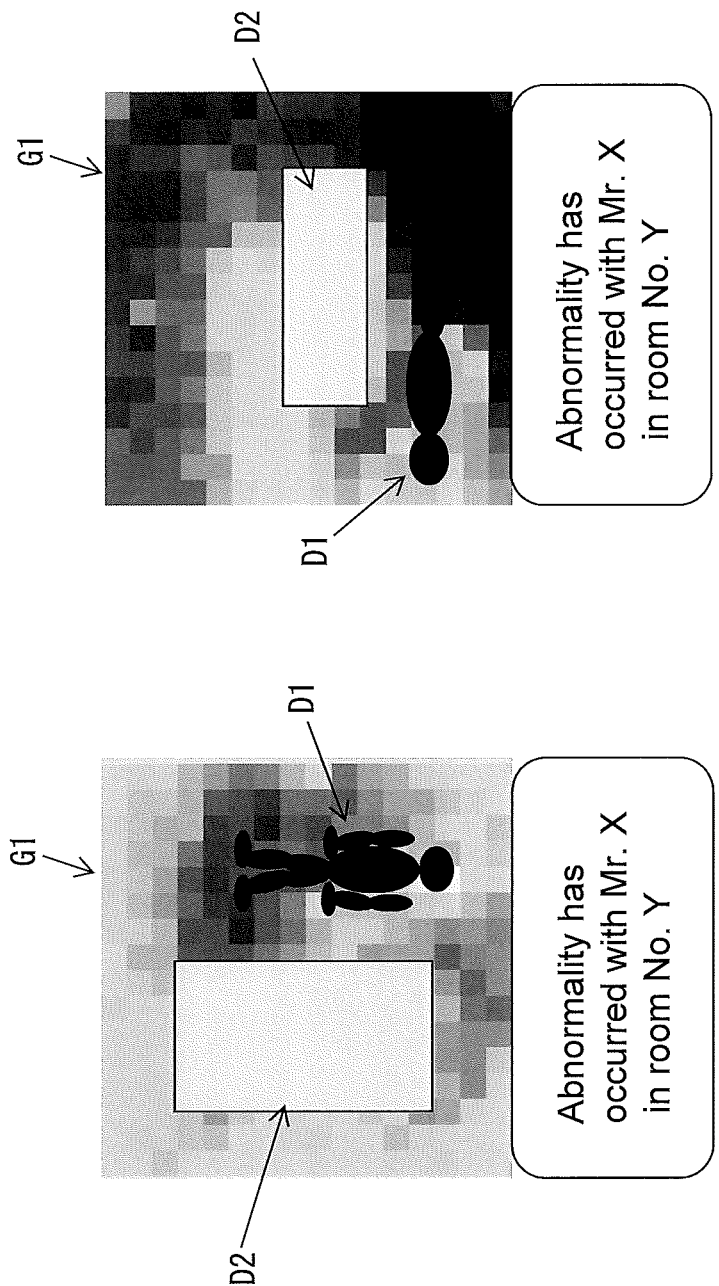
FIGS. 25A and 25B are diagrams of a display that combines text information with a rolled-over recumbent image (emergency) on the display device whose display is controlled by the display control device according to yet another embodiment of the present invention.

For instance, as shown in FIGS. 25A and 25B, text information such as "abnormality has occurred with Mr. X in room No. Y" may be displayed together with the image information.

In this case, the urgency of the care can be displayed in a way that is more easily understandable to the caregiver.

This text information may consist of a plurality of sets of text information corresponding to the determination result by the determination component that determines the how urgently the care receiver needs care, with this information stored ahead of time in the storage component 14 or the like.

(D)

In the above embodiment, as shown in FIG. 2, an example was described in which the infrared array sensors 21a and 21b were provided on the ceiling and the wall as the first and second image sensors, but the present invention is not limited to this.

For example, an image sensor may be provided on just the ceiling, or just on the wall, an image sensor for imaging the human body from an angle may be used.

However, in order to determine the body orientation correctly, it is preferable to adopt a configuration as in the above embodiment, in which a image sensors are provided on both the ceiling and the wall.

(E)

In the above embodiment, an example was described in which the infrared array sensors 21a and 21b that sensed the temperature distribution were used as image sensors for transmitting images to the image acquisition component 11, but the present invention is not limited to this.

For example, it is also possible to use other image sensors, such as a surveillance camera or a distance sensor, as the image sensors.

(F)

In the above embodiment, an example was described in which the display controller 10 and the display control system 20 of the present invention were applied to monitoring in a care facility or the like where a plurality of care receivers P1 are cared for, but the present invention is not limited to this.

For example, in addition to nursing facilities, the present invention may also be applied to a facility such as a hospital or the like in which disabled people or elderly people live.

Alternatively, the present invention may be applied to the monitoring of elderly people who are living alone.

In this case, mobile terminals own by the children who live apart from the elderly people can be used as a display device, allowing the monitoring to be carried out from a remote location.

INDUSTRIAL APPLICABILITY

The display control device of the present invention has the effect of allowing a situation in which a care receiver is in need of care, for example, to be properly recognized by a caregiver, and therefore can be widely applied to various kinds of device used for monitoring seniors, children, pets, and so forth.

REFERENCE SIGNS LIST 10 display control device
11 image acquisition component
12 orientation estimation component
13 controller
14 storage component
15 determination component
16 count estimation component
20 display control system
21a infrared array sensor (first image sensor) (ceiling)
21b infrared array sensor (second image sensor) (side)
22 display device
22a host computer (display device)
22b mobile terminal (display device)
30 room
30a ceiling
30b wall
31 bed
32 wheelchair
33 shelf
110 display control device
114 cloud space
120 display control system
G1 infrared image (image)
G1a flickering region
G1b heat source expansion region
D1 dummy image (caregiver) (first dummy image)
D2 dummy image (bed) (second dummy image)
D3 dummy image (blanket) (second dummy image)
D4 dummy image (wheelchair) (second dummy image)
P1 care receiver (person)

The invention claimed is:

1. A display control device comprising:
    an image acquisition component configured to acquire image data sensed by an image sensor installed in a room;
    an orientation estimation component configured to estimate the orientation of a person in the room on the basis of the image data acquired by the image acquisition component; and
    a controller configured to control a display device so that a first dummy image, which shows a simplified view of the orientation of the person estimated by the orientation estimation component, is displayed superimposed over the image data, and
    a determination component configured to determine a care urgency level according to an amount of flickering of an image near the person in the image data by referring to the plurality of pieces of image data continuously acquired by the image acquisition component, and
    the controller superimposes and displays the head or face portion of the first dummy image, using as a reference the position of the head or face of the person included in the image data.

2. The display control device according to claim 1, further comprising:
    a storage component configured to store a plurality of the first dummy images in a state of being associated with orientations of the person.

3. The display control device according to claim 1,
    wherein the image sensor is an infrared sensor configured to acquire a thermal image, and
    the determination component makes a determination according to the degree of fluctuation in the position of the thermal center of gravity in an area near the person in the thermal image continuously acquired by the infrared sensor.

4. The display control device according to claim 1,
    wherein the image sensor is an infrared sensor configured to acquire a thermal image, and
    the determination component makes a determination by detecting enlargement of a heat source in an area near the person in the thermal image continuously acquired by the infrared sensor.

5. The display control device according to claim 1, further comprising
    a count estimator configured to estimate the number of people included in the image data acquired by the image acquisition component.

6. The display control device according to claim 5,
    wherein the controller performs display control of the display device when it is determined by the count estimator that the number of people in the image data is one.

7. The display control device according to claim 1, wherein the controller changes a color of the first dummy image on the display device according to an estimation result produced by the orientation estimation component.

8. The display control device according to claim 1, wherein the controller flashes the first dummy image on the display device according to an estimation result produced by the orientation estimation component.

9. The display control device according to claim 1, wherein the controller displays the first dummy image superimposed over the image data and displays an emergency message on the display device, according to the estimation result produced by the orientation estimation component.

10. The display control device according to claim 1, wherein the orientation estimation component estimates the orientation by using detection results produced by the plurality of the image sensors, which detect a person who is the room from different directions.

11. The display control device according to claim 1, wherein the controller displays the first dummy image, corresponding to at least one of a standing position, a seated position, a supine position, a lateral recumbent position, a prone position, and a half-sitting position of the person, superimposed over the image data.

12. The display control device according to claim 1, wherein the controller displays a second dummy image corresponding to furniture and equipment installed in the room so as to be superimposed with the locations of the furniture and the equipment in the image data.

13. A display control system, comprising:
the display control device according to claim 1; and
an image sensor configured to supply the image data to the image acquisition component.

14. The display control system according to claim 13, further comprising
a display device whose display is controlled by the controller of the display control device.

15. The display control system according to claim 14, wherein the display device includes the display device of a host terminal used by the caregiver who cares for the person who is in the room, or a portable terminal owned by the caregiver.

16. The display control system according to claim 1, wherein the image sensor includes:
a first image sensor configured to detect the person from above in the room; and
a second image sensor configured to detect the person from a side.

17. The display control system according to claim 1, wherein the image sensor is either an infrared array sensor or a distance sensor.

18. A display control method, comprising:
acquiring image data sensed by an image sensor installed in a room;
estimating the orientation of a person in the room on the basis of the image data acquired in the image acquisition step;
controlling a display device so that a first dummy image, which shows a simplified view of the orientation of the person estimated in the orientation estimation step, is displayed superimposed over the image data, and superimposing and displaying the head or face portion of the first dummy image, using as a reference the position of the head or face of the person included in the image data; and
determining a care urgency level according to an amount of flickering of an image near the person in the image data by referring to the plurality of pieces of image data continuously acquired.

19. A non-transitory computer-readable storage medium that stores a display control program for causing a computer to execute a display control method, the display control method comprising:
acquiring image data sensed by an image sensor installed in a room;
estimating the orientation of a person in the room on the basis of the acquired image data;
controlling a display device so that a first dummy image, which shows a simplified view of the estimated orientation of the person, is displayed superimposed over the image data, and superimposing and displaying the head or face portion of the first dummy image, using as a reference the position of the head or face of the person included in the image data; and
determining a care urgency level according to an amount of flickering of an image near the person in the image data by referring to the plurality of pieces of image data continuously acquired.

* * * * *